(12) United States Patent
Hagy et al.

(10) Patent No.: US 10,537,302 B2
(45) Date of Patent: Jan. 21, 2020

(54) NEEDLE GUIDANCE SYSTEMS FOR USE WITH ULTRASOUND DEVICES

(71) Applicant: Soma Access Systems, LLC, Englewood, CO (US)

(72) Inventors: M. Dexter Hagy, Greenville, SC (US); Stephen F. Ridley, Columbia, SC (US)

(73) Assignee: Soma Research, LLC, Greenville, SC (US)

( * ) Notice: Subject to any disclaimer, the term of this patent is extended or adjusted under 35 U.S.C. 154(b) by 1122 days.

(21) Appl. No.: 14/593,404

(22) Filed: Jan. 9, 2015

(65) Prior Publication Data

US 2015/0245872 A1 Sep. 3, 2015

Related U.S. Application Data

(60) Provisional application No. 61/925,798, filed on Jan. 10, 2014.

(51) Int. Cl.
*A61B 8/00* (2006.01)
*A61B 8/08* (2006.01)
*A61B 17/34* (2006.01)

(52) U.S. Cl.
CPC ............. *A61B 8/0841* (2013.01); *A61B 8/44* (2013.01); *A61B 8/4411* (2013.01); *A61B 8/4422* (2013.01); *A61B 8/4438* (2013.01); *A61B 8/461* (2013.01); *A61B 17/3403* (2013.01); *A61B 2017/3413* (2013.01)

(58) Field of Classification Search
CPC ...................... A61M 25/0017; A61M 25/0111
See application file for complete search history.

(56) References Cited

U.S. PATENT DOCUMENTS

| | | | |
|---|---|---|---|
| 4,635,644 A | 1/1987 | Yagata | |
| 4,838,506 A | 6/1989 | Cooper | |
| 5,924,992 A | 7/1999 | Park et al. | |
| 6,589,164 B1 * | 7/2003 | Flaherty | A61M 25/0017 600/121 |
| 6,884,219 B1 | 4/2005 | Pruter | |
| 6,908,433 B1 | 6/2005 | Pruter | |

(Continued)

FOREIGN PATENT DOCUMENTS

| | | |
|---|---|---|
| EP | 0 448 222 | 9/1991 |
| JP | 11128237 | 5/1999 |

(Continued)

OTHER PUBLICATIONS

Extended European Search Report; dated May 26, 2017.

(Continued)

*Primary Examiner* — Joseph M Santos Rodriguez
(74) *Attorney, Agent, or Firm* — Dority & Manning, P.A.

(57) ABSTRACT

Ultrasound devices and guidance systems for ultrasound devices for subdermal devices (e.g., needles) used in conjunction with the ultrasound devices are described. The guidance systems can includes features for easy release of a device from the system following targeting to a subdermal site. A guidance system can be ambidextrous such that a needle can be released by use of either the left or right hand and by use of either a thumb or a finger of an operator. Embodiments that include guidance tracks and slidable guidance cartridges that grasp the hub of a subdermal device are also described.

26 Claims, 18 Drawing Sheets

(56) References Cited

U.S. PATENT DOCUMENTS

| | | | |
|---|---|---|---|
| 7,244,234 B2 | 7/2007 | Ridley et al. | |
| 7,405,132 B2 | 7/2008 | Arao et al. | |
| 7,588,541 B2 | 9/2009 | Floyd et al. | |
| 8,147,408 B2 | 4/2012 | Bunce et al. | |
| 8,152,724 B2 | 4/2012 | Ridley et al. | |
| 8,303,607 B2 | 11/2012 | Suzuki et al. | |
| 8,388,541 B2 | 3/2013 | Messerly et al. | |
| 8,425,425 B2 | 4/2013 | Hagy et al. | |
| 8,496,592 B2 | 7/2013 | Ridley et al. | |
| 8,761,862 B2 | 6/2014 | Ridley et al. | |
| 8,900,151 B2 | 12/2014 | Ridley et al. | |
| 9,681,823 B2 | 6/2017 | Messerly et al. | |
| 2002/0133079 A1 | 9/2002 | Sandhu | |
| 2007/0049822 A1 | 3/2007 | Bunce et al. | |
| 2007/0073155 A1 | 3/2007 | Park et al. | |
| 2008/0015624 A1* | 1/2008 | Sonoda | A61M 5/158 606/185 |
| 2010/0041990 A1 | 2/2010 | Schlitt et al. | |
| 2010/0081920 A1 | 4/2010 | Whitmore, III et al. | |
| 2010/0228182 A1* | 9/2010 | Clark, III | A61B 18/1477 604/21 |
| 2012/0071759 A1* | 3/2012 | Hagy | A61B 8/0841 600/443 |
| 2012/0157849 A1 | 6/2012 | Ridley et al. | |
| 2012/0259219 A1 | 10/2012 | Sheldon et al. | |
| 2013/0041254 A1 | 2/2013 | Hagy et al. | |
| 2013/0102901 A1 | 4/2013 | Ridley et al. | |
| 2013/0131597 A1 | 5/2013 | Blaivas et al. | |
| 2013/0338477 A1 | 12/2013 | Glossop et al. | |
| 2014/0275990 A1 | 9/2014 | Hagy et al. | |
| 2015/0245809 A1 | 9/2015 | Hagy et al. | |

FOREIGN PATENT DOCUMENTS

| | | |
|---|---|---|
| WO | WO 2005/046444 A2 | 5/2005 |
| WO | WO2006/060657 | 6/2006 |
| WO | WO 2011/043874 A1 | 4/2011 |
| WO | WO 2011/043875 A2 | 4/2011 |
| WO | WO 2012/040077 A1 | 3/2012 |
| WO | WO 2014/143650 A1 | 9/2014 |

OTHER PUBLICATIONS

Soma Access Systems, LLC, International Patent Application No. PCT/US2015/010799; International Search Report and Written Opinion; dated May 4, 2015; (10 pages).

Soma Access Systems, LLC, International Patent Application No. PCT/US2015/010801; International Search Report and Written Opinion; dated May 4, 2015; (9 pages).

* cited by examiner

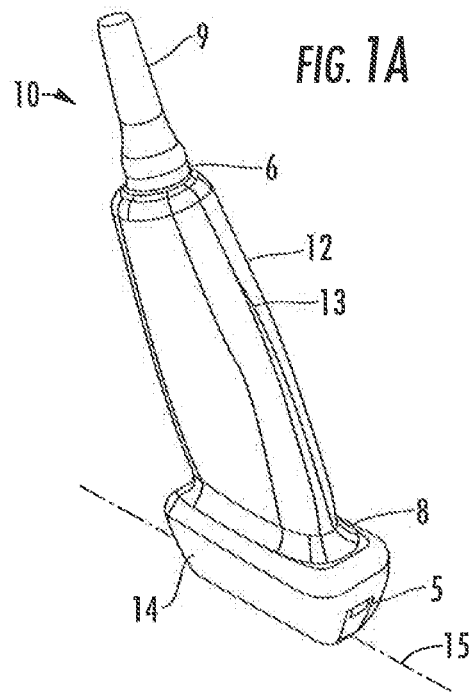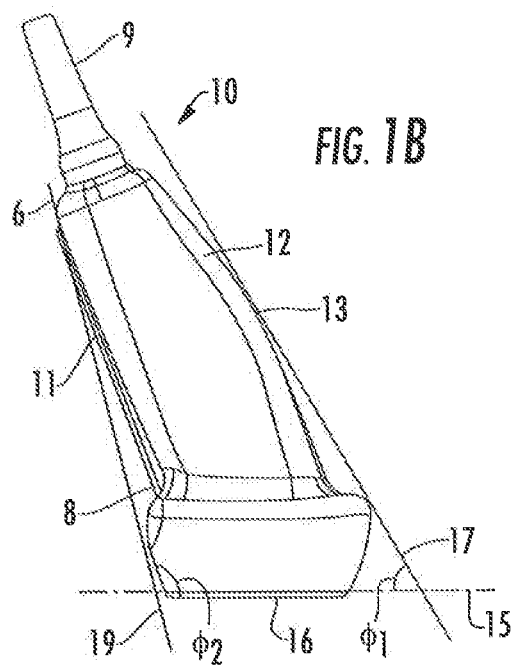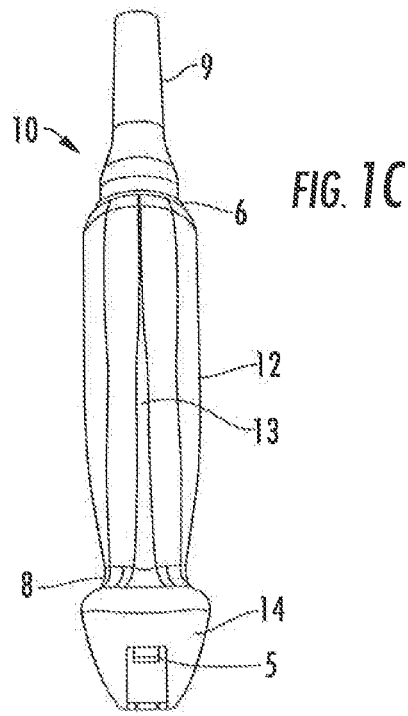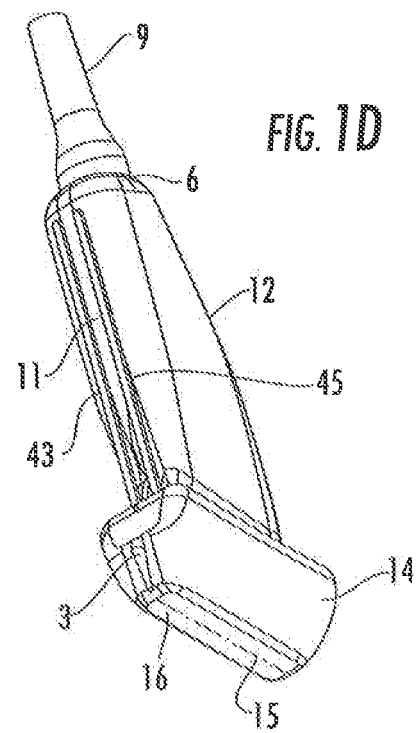

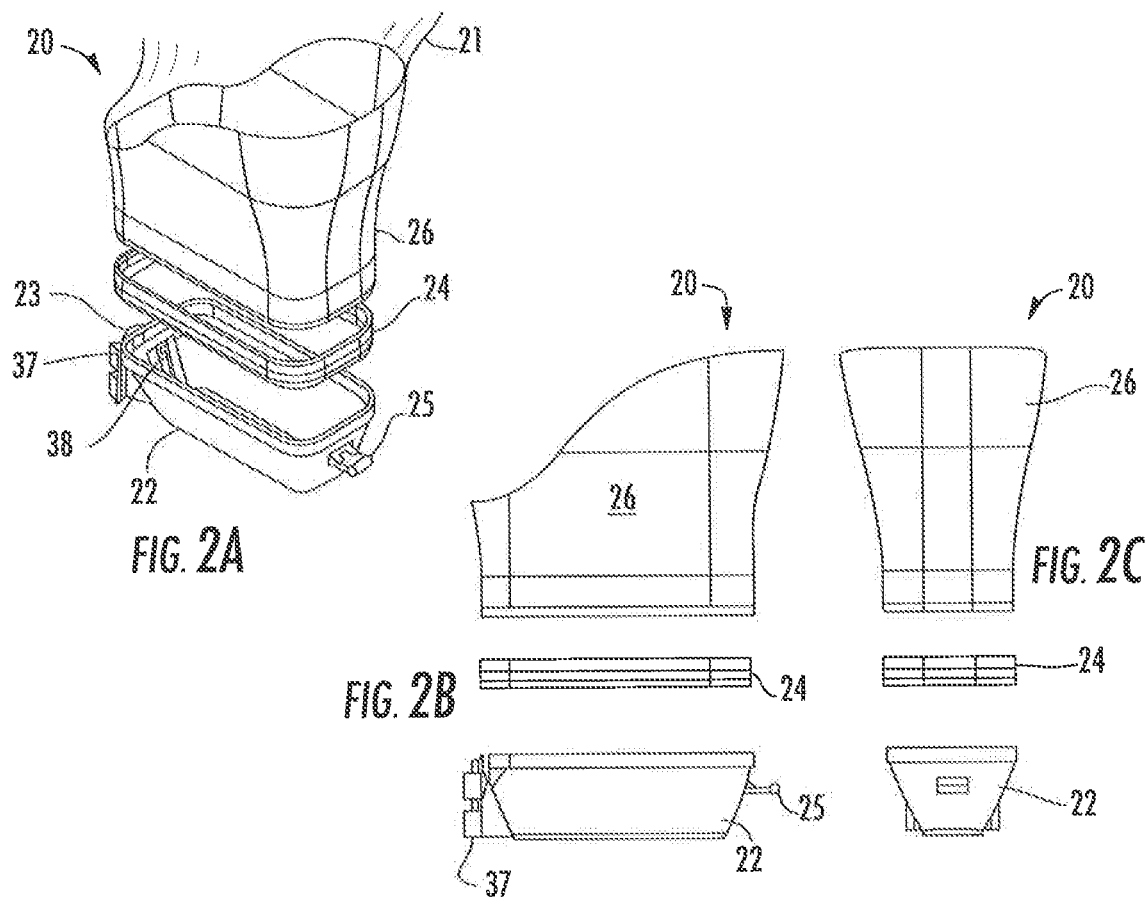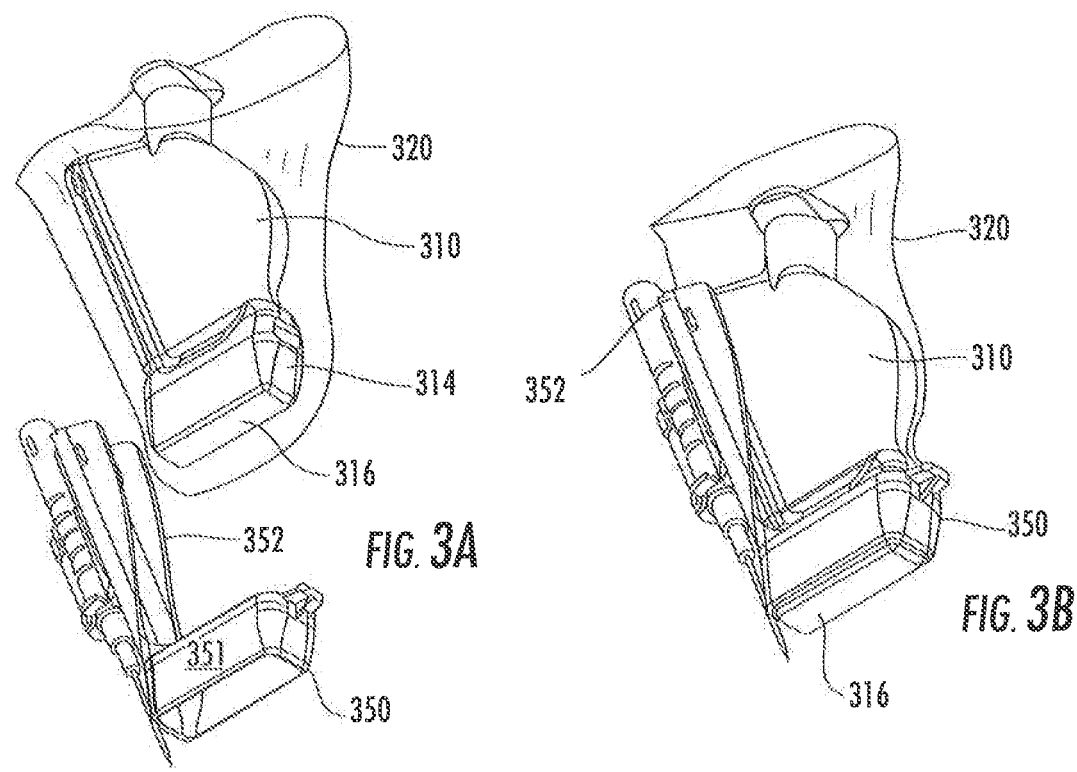

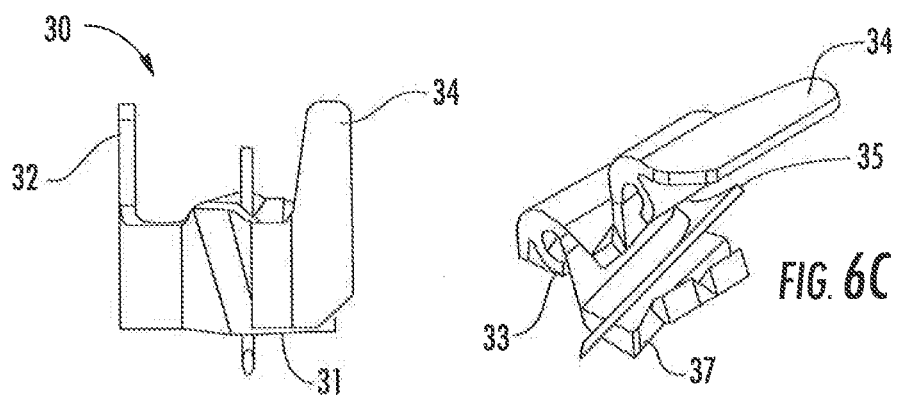
FIG. 6A
FIG. 6C
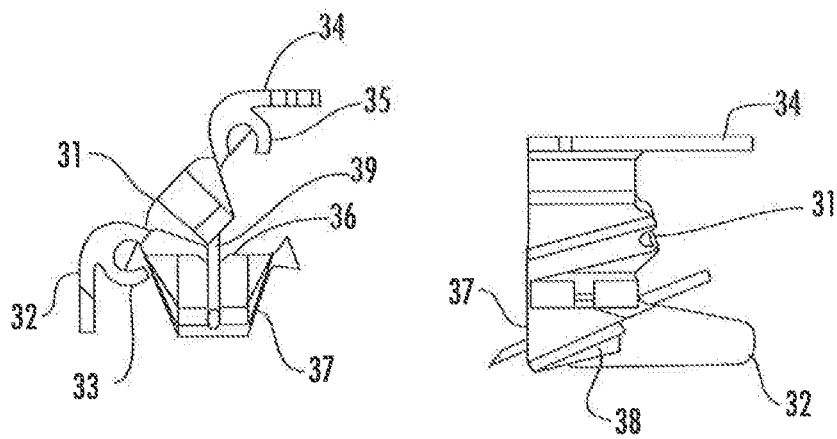
FIG. 6B
FIG. 6D

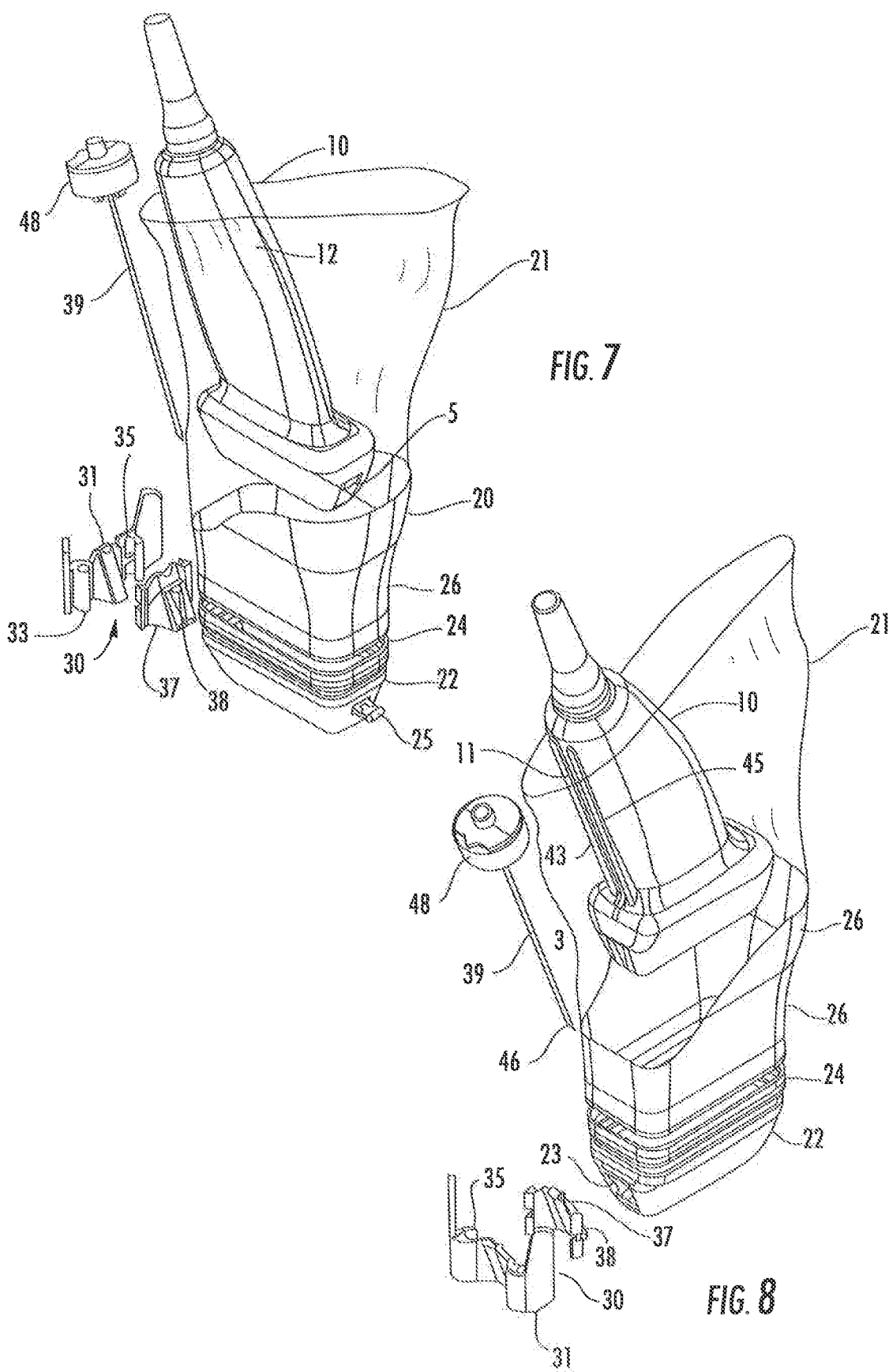

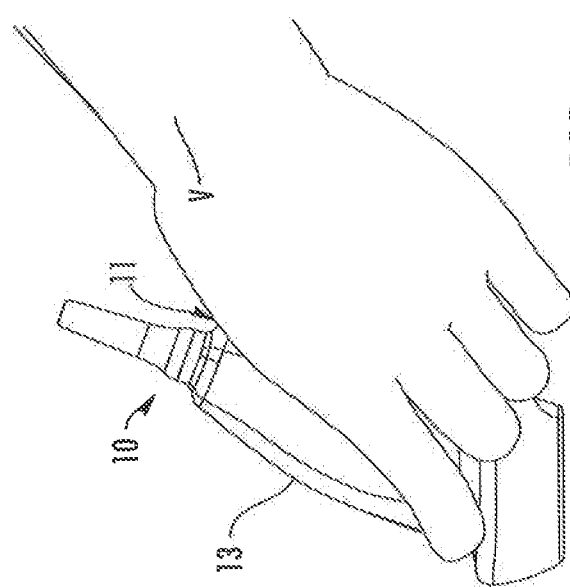
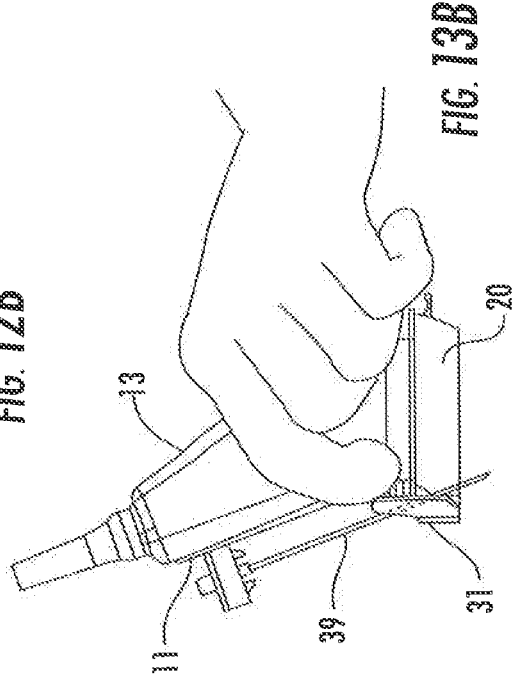
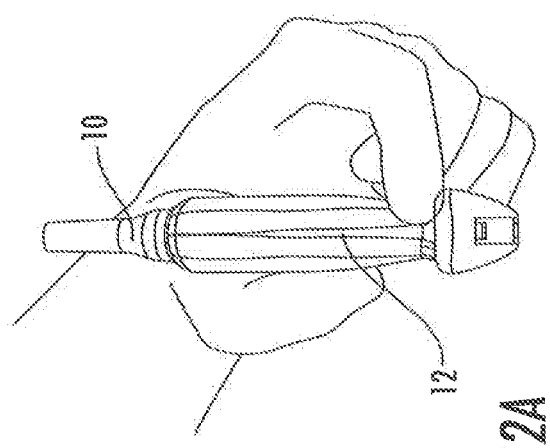
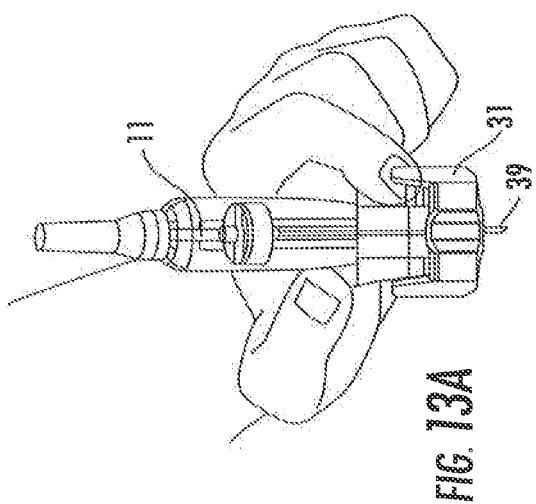

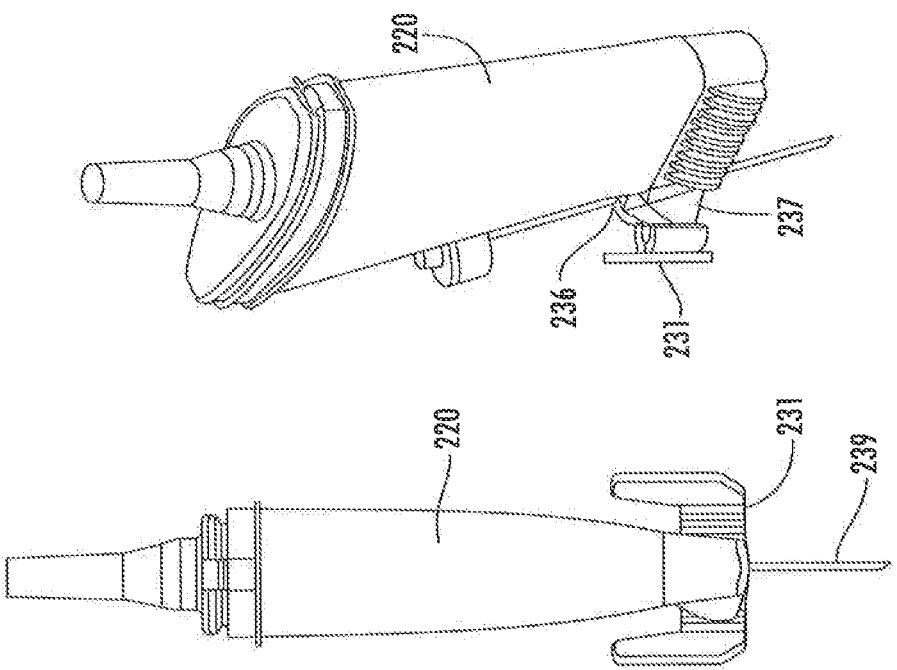
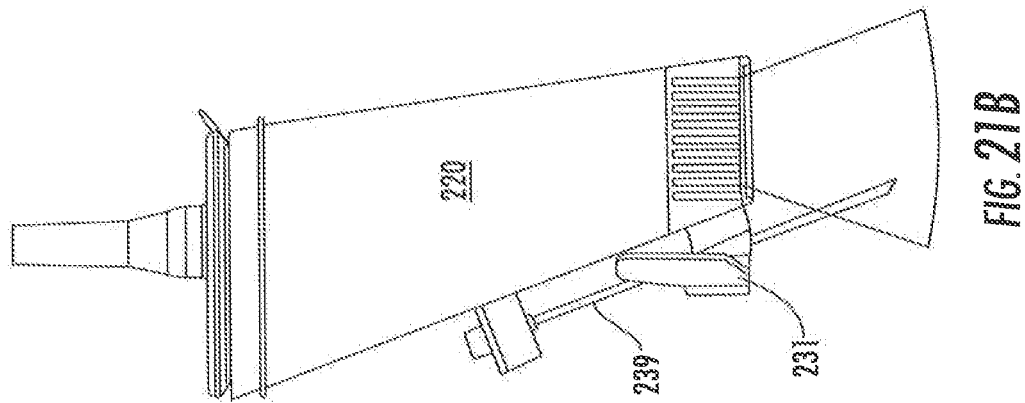
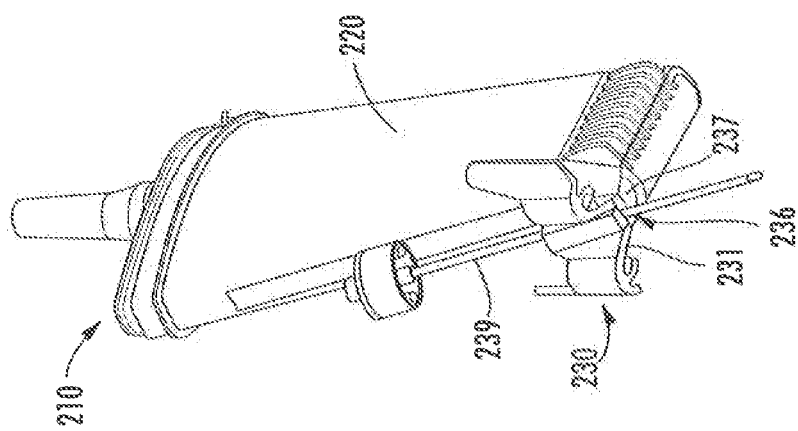

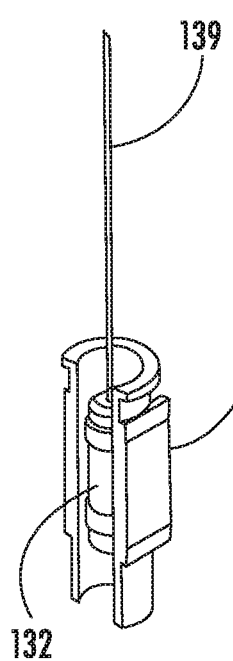 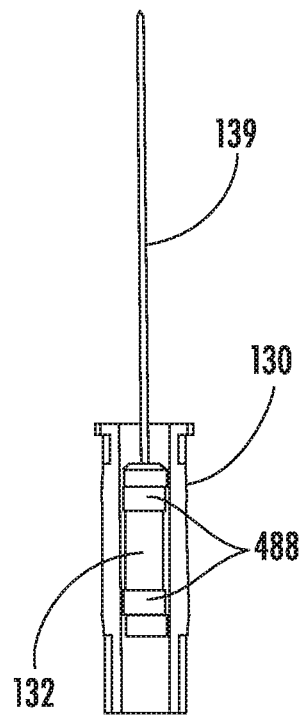 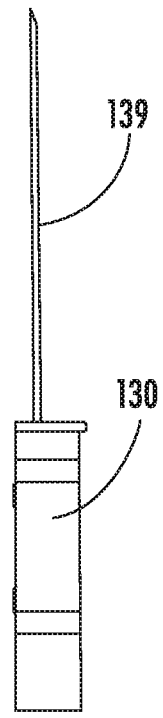
FIG. 22A  FIG. 22B  FIG. 22C
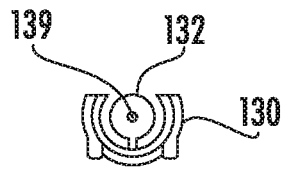
FIG. 22D

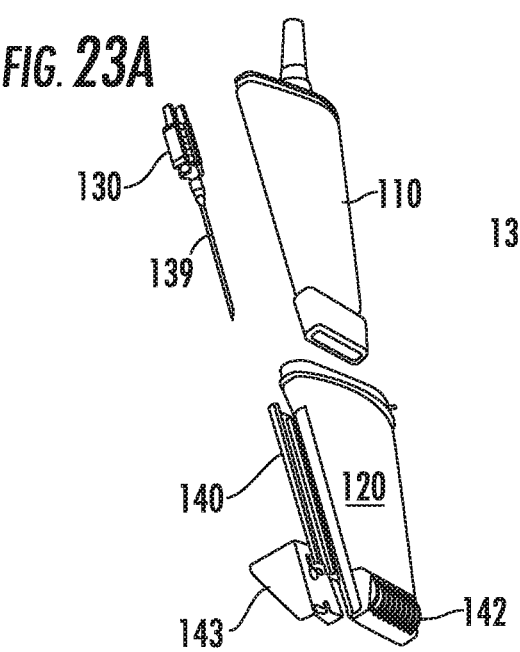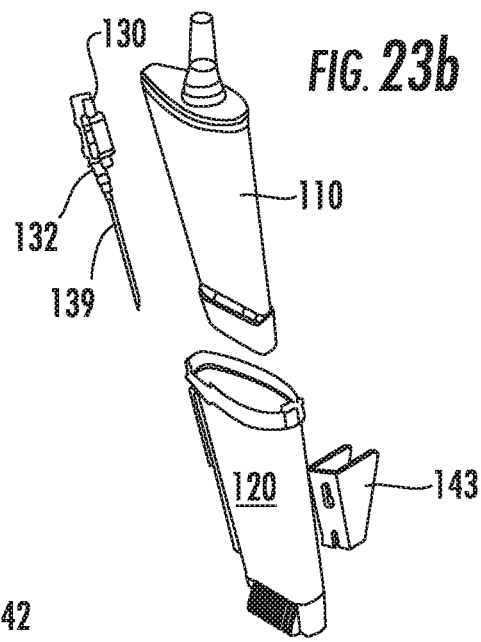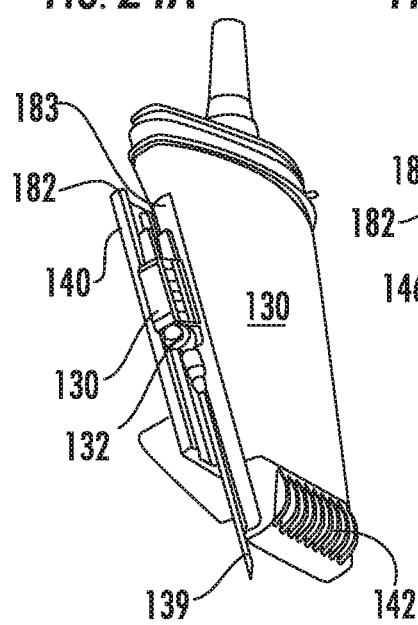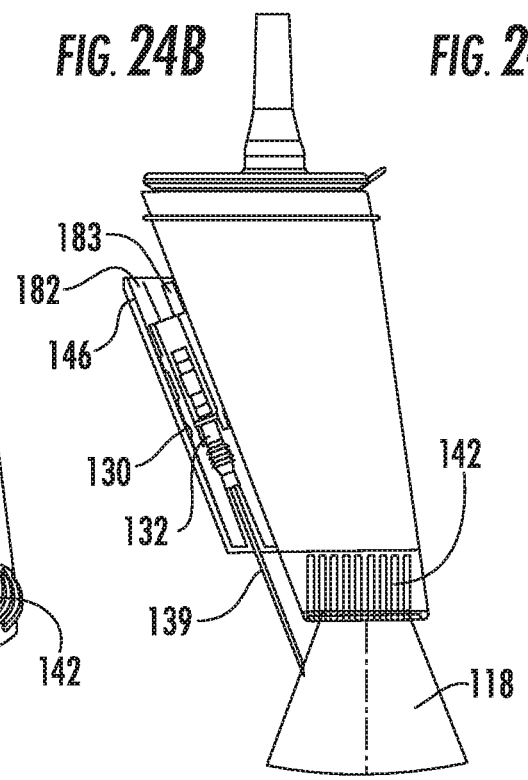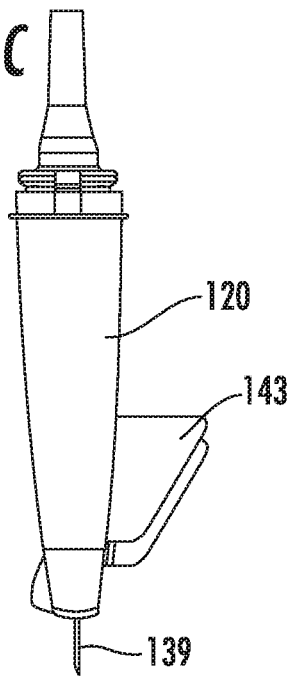

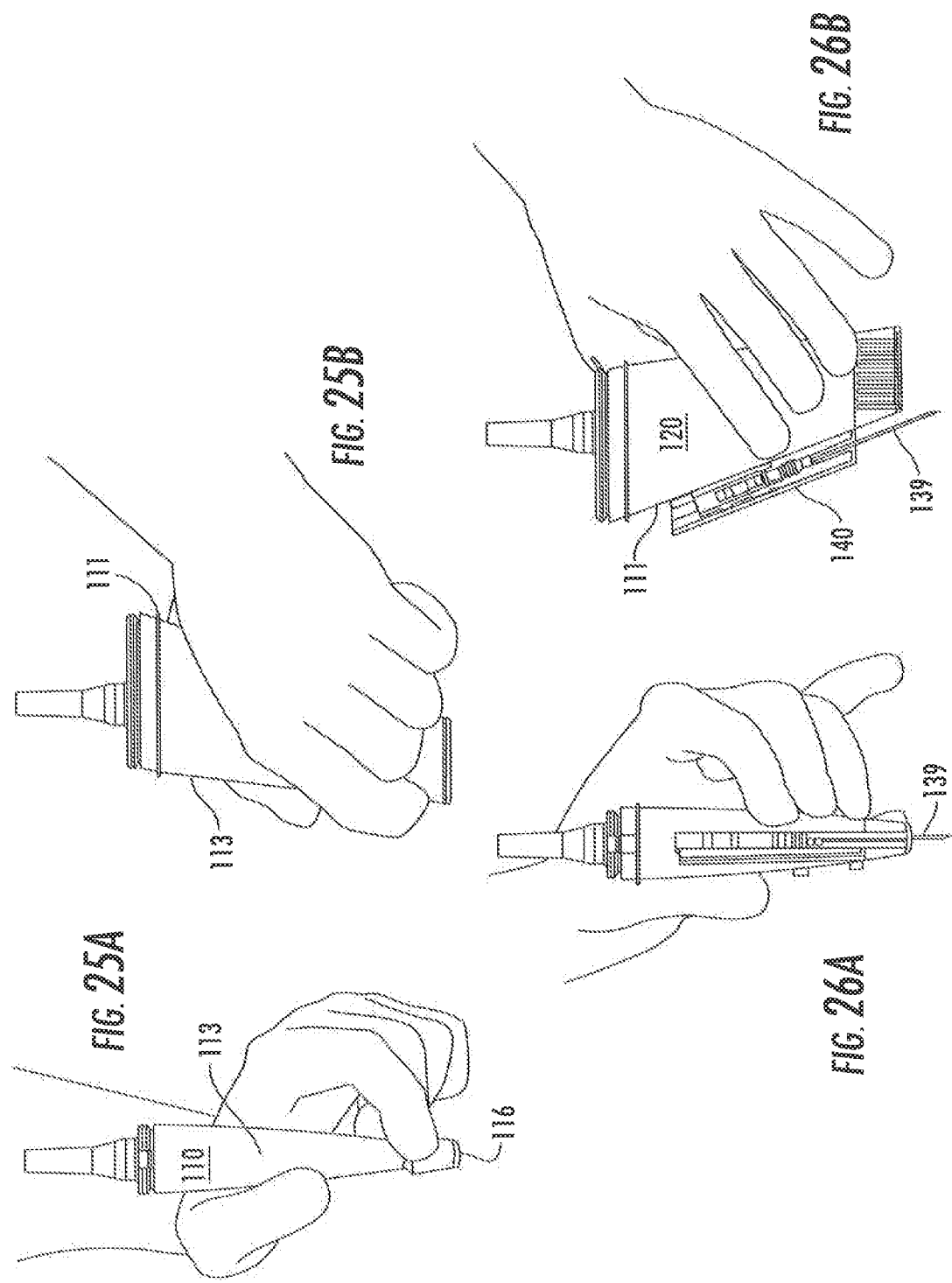

NEEDLE GUIDANCE SYSTEMS FOR USE WITH ULTRASOUND DEVICES

CROSS REFERENCE TO RELATED APPLICATION

This application claims filing benefit of U.S. Provisional Patent Application Ser. No. 61/925,798 having a filing date of Jan. 10, 2014 entitled "Ergonomic Multi-Mode Ultrasound Device," which is incorporated herein by reference.

BACKGROUND

Ultrasound devices are utilized for visualization in many different medical applications, including both diagnostic and procedural applications. Diagnostic applications include those in which internal structures are merely visualized by use of an ultrasound device. Ultrasound guided procedural applications combine the visualization capability of the ultrasound device with invasive techniques such as catheterization, centesis, and biopsy procedures that involve the placement of a subdermal device, e.g., a needle, within a subject.

The proper placement of subdermal devices during procedural applications presents difficulties. For instance, proper insertion and placement of a subdermal device such as a needle depends on correct localization of anatomical landmarks, proper positioning of the subject in relation to the care provider, and awareness of both the depth of the subdermal target and the angle of the device insertion. Risks of unsuccessful placement of a subdermal device can range from minor complications, such as patient anxiety and discomfort due to repetition of the procedure following incorrect initial placement, to severe complications, such as pneumothorax, arterial or venous laceration, or delay of delivery of life-saving fluids or medications in an emergency situation.

What are needed in the art are improved ultrasound devices and systems as well as methods for using the devices and systems. For instance, what are needed in the art are guidance systems that can be utilized to accurately guide a a subdermal device during a procedural application.

SUMMARY

According to one embodiment, disclosed is a system for use in conjunction with an ultrasound device. For instance, a system can include one or more guide rails that lay along a length of a track. For instance, the track can be on a length of a sterilizable shield for use in conjunction with an ultrasound device or another component of a system for use with an ultrasound device. The system also includes a guide cartridge capable of being held in conjunction with the guide rail such that the guide cartridge is in slidable conformation with the track, i.e., the guide cartridge is capable of sliding from a first end of the track to a second end of the track. The guide cartridge is also removably attachable to a hub of a subdermal device and can hold the device as the tip of the device is targeted to an internal site of a patient.

Methods for using the systems are also described.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 1 illustrates one embodiment of a multi-mode ultrasound device including a first perspective view (FIG. 1A), a side view (FIG. 1B), a front view (FIG. 1C), and a second perspective view (FIG. 1D).

FIG. 2 illustrates a sterilizable shield that may be utilized in conjunction with an ultrasound device including a perspective view (FIG. 2A), a side view (FIG. 2B), and a front view (FIG. 2C).

FIG. 3 illustrates another embodiment of a sterilizable shield including an exploded view (FIG. 3A) and a combined view (FIG. 3B).

FIG. 6 illustrates the ambidextrous needle guide of FIG. 4 in an open configuration following opening from the second side of the guide including a front view (FIG. 6A), a top view (FIG. 6B), a perspective view (FIG. 6C), and a side view (FIG. 6D).

FIG. 7 illustrates a perspective exploded view of a system including the device of FIG. 1, the sterilizable shield of FIG. 2, and the ambidextrous needle guide of FIG. 4.

FIG. 8 illustrates another perspective exploded view of the system of FIG. 7.

FIG. 12 illustrates one possible orientation of an ultrasound device as illustrated in FIG. 1 during a diagnostic application including a front view (FIG. 12A) and a side view (FIG. 12B).

FIG. 13 illustrates one possible orientation of a system during a procedural application including a front view (FIG. 13A) and a side view (FIG. 13B).

FIG. 21 illustrates a first perspective view (FIG. 21A), a side view (FIG. 21B), a front view (FIG. 21C), and a second perspective view (FIG. 21D) of a system as described herein.

FIG. 22 illustrates track-based guidance system components including a perspective view (FIG. 22A), a front view (FIG. 22B), a side view (FIG. 22C), and a top view (FIG. 22D).

FIG. 23 illustrates two perspective exploded views (FIG. 23A, FIG. 23B) of a track-based guidance system in conjunction with a sterilizable shield and an ultrasound device.

FIG. 24 illustrates a track-based guidance system including a perspective view (FIG. 24A), a side view (FIG. 24B), and a front view (FIG. 24C).

FIG. 25 illustrates one possible orientation of an ultrasound device during a diagnostic application including a front view (FIG. 25A) and a side view (FIG. 25B).

FIG. 26 illustrates one possible orientation of a track-based guidance system during a procedural application including a front view (FIG. 26A) and a side view (FIG. 26B).

Figure 4A:
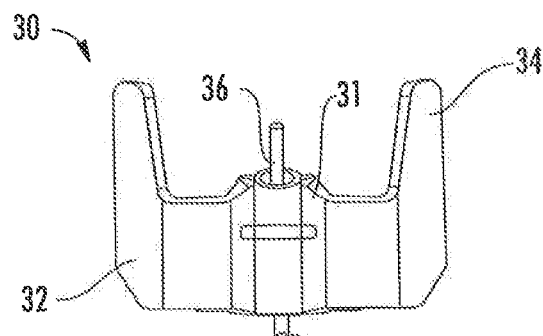
FIG. 4 illustrates an ambidextrous needle guide that may be utilized in conjunction with the sterilizable shield of FIG. 2 including a front view (FIG. 4A), a top view (FIG. 4B), a perspective view (FIG. 4C), and a side view (FIG. 4D).
Figure 4C:
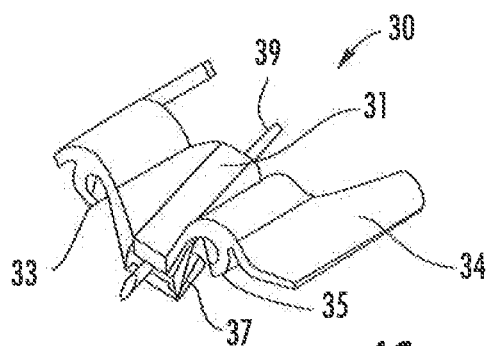
Figure 4B:
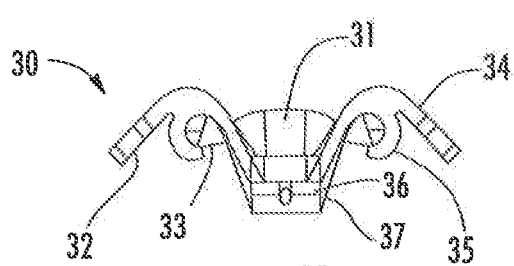

Repeat use of reference characters in the present specification and drawings is intended to represent the same or analogous features of elements of the disclosed subject matter. Other objects, features and aspects of the subject matter are disclosed in or are obvious from the following detailed description.

DETAILED DESCRIPTION OF PREFERRED EMBODIMENTS

Reference will now be made in detail to various embodiments of the disclosed subject matter, one or more examples of which are set forth below. Each embodiment is provided by way of explanation of the subject matter, not limitation of the subject matter. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment. Thus, it is intended that the present disclosure cover such modifications and variations as come within the scope of the appended claims and their equivalents.

In general, disclosed herein are guidance systems for ultrasound devices that can be utilized for both diagnostic and procedural applications. In one embodiment, the ultrasound devices can have an ergonomic design and can be held in a different orientation depending upon the type of application that is being carried out. As such, the device can be held in a comfortable position by the operator in both diagnostic and procedural applications. More comfortable and ergonomic orientations can provide improved stability to the device during use. Improved stability can lead to improved visualization and, in the case of procedural applications, less error in placement of subdermal devices. The guidance systems for use with the ultrasound devices can provide for easy use and accurate targeting as well as simple separation of a subdermal device from the placement/ultrasound system following guidance of the subdermal device to the target.

As utilized herein, the term "ultrasound device" generally refers to a housing that incorporates an ultrasound transducer therein as well as any hardware and software associated with the transducer and housing. In one embodiment, the ultrasound device can be utilized in conjunction with a subdermal device such as a needle, but does not necessarily include the subdermal device itself. For instance, an ultrasound device can include a needle guide as an attachable or permanent component of the ultrasound device, and a needle can be utilized in conjunction with the ultrasound device to access a subdermal site by guiding the needle through the needle guide of the ultrasound device.

As utilized herein, the term "subdermal device" generally refers to a component that can be guided to an internal site, for instance for delivery of a therapeutic (e.g., a compound or other treatment) to the location; for removal of material from the location; and so forth. For example, the term "subdermal device" can refer to a needle, a tube, a biopsy needle or blade, or any other item that can be guided to a subdermal location. In general, a subdermal device (also synonymous with the term "subcutaneous device") can be guided by and used in conjunction with an ultrasound device as described herein. In one embodiment, a subdermal device can define a ratio of the length of the device to the diameter (or a width) of the device greater than about 10. Moreover, a subdermal device can define any cross sectional shape, e.g., round, square, oblong, triangular, rectangular, etc.

In one embodiment, an ultrasound device can include a detection system that can be utilized during procedural applications for detecting and visualizing the subdermal device. A detection system can include a detector that is removably or permanently attached to the ultrasound device or a component of the system and that can recognize the location and/or motion of a subdermal device, e.g. a needle, during the procedure. During the procedure, the needle is guided such that the needle tip approaches a targeted subdermal site that can be visualized on a sonogram that is created from a plane of sound waves emitted by the ultrasound transducer. Specifically, the needle is guided along a path that has a known correlation with the plane of the sound waves emitted by the ultrasound transducer, e.g., coincident in the scanned plane, parallel to the scanned plane, or intersecting the scanned plane at a point. The detector can register the location and/or motion of the needle as it passes the detector on the ultrasound device and as the needle tip proceeds into the subject. The detector can be in communication with a processor that can utilize information received from the detector with regard to location of the needle and accurately identify the location of the needle tip in real time based upon that information. A processor can also be in communication with a monitor and can create an image of a virtual needle on the monitor from the information received from the motion detector. The virtual needle image can then be overlaid on the sonogram in real-time and portray the motion of the needle tip as it approaches the subdermal target. The system can accurately correlate the location of the virtual needle tip as determined by use of the detector with the location of the actual needle tip that is in the subject and provide real-time visualization of the entire procedure on the ultrasound. Such detection mechanisms and methods have been described, for instance in U.S. Pat. Nos. 8,496,592; 8,425,425; 8,152,724; and 7,244,234, all of which are incorporated herein by reference.

One embodiment of a multi-mode ergonomic ultrasound device 10 is illustrated in FIG. 1, which includes a first perspective view (FIG. 1A), a side view (FIG. 1B), a front view (FIG. 1C), and a second perspective view (FIG. 1D). The device 10 includes a handle 12 and a base 14. The base can include the skin contacting surface 16 that will be either directly or indirectly held against the skin of a subject during use. For instance, when the device 10 is utilized in conjunction with a sterilizable shield, discussed further below, the sterilizable shield may be located between the skin contacting surface 16 and a subject's skin to provide a sterile barrier between the device 10 and the subject. The skin contacting surface 16 will indirectly contact the subject's skin in this case. The base 14 of the device can generally contain the ultrasound transducer (not shown in FIG. 1).

Any type of ultrasound transducer as is generally known in the art can be incorporated in transducer device 10 that can emit ultrasonic waves and receive the reflection of the emitted ultrasonic waves. By way of example, a piezoelectric transducer formed of one or more piezoelectric crystalline materials arranged in a one or two-dimensional array can be utilized. For instance, a one dimensional array including a series of elements in a line can be used to create a two-dimensional image. Alternatively, a single transmitter can be moved through space to create two-dimensional image. A two-dimensional array can include a matrix of elements in a plane and can be used to create a three-dimensional image. A three-dimensional image can also be made by moving a two-dimensional array through space (rotationally or otherwise). Transducer materials generally include ferroelectric piezoceramic crystalline materials such as lead zirconate titanate (PZT), although other suitable materials are encompassed herein, such as CMUT/PMUT materials.

An ultrasound transducer can be formed of multiple elements. However, single transmitter/receiver devices are also encompassed by the present disclosure. The use of a multiple element ultrasound transducer can be advantageous in certain embodiments, as the individual elements that make up the array can be individually controlled. Such control systems are generally known in the art and thus will not be described in detail.

The ultrasound transducer can be located within the base 14 such that an ultrasonic wave emitted from the device will pass through the skin contacting surface 16 and into a subject. The ultrasonic wave will generally pass through the skin contacting surface along a line 15 as shown in FIG. 1D. Line 15 has been extended on FIG. 1A and FIG. 1B for clarity.

The shape of all or a portion of an ultrasound device 10 may be particularly designed to fit specific locations of the anatomy. For example, the skin contacting surface 16 may be shaped to be utilized specifically for infraclavicular approach to the subclavian vein, approach to the internal jugular vein, specific biopsy procedures including, without limitation, breast biopsy, thyroid nodule biopsy, prostate biopsy, lymph node biopsy, and so forth, or some other specific use. Variations in shape for any particular application can include, for example, a specific geometry for the footprint of a skin contacting surface 16.

The handle 12 of the device 10 includes a first side 13 and a second side 11 that are opposite each other as shown. The handle also includes a proximal end 8 where the handle 12 meets the base 14 and an opposite distal end 6. While the first side 13 is represented as the "front" of the device in the front view FIG. 1C, the device does not actually have a permanently defined "front" and "back" as the device can be held in a different orientation depending upon the application as illustrated and explained in further detail herein.

The handle 12 of the device 10 is set so as to be angled with the base 14, which can provide an ergonomic design for both the procedural and diagnostic applications. For instance, the angle that each side of the device need not be the same on the first and second sides 13, 11 of the device, which can improve the ergonomic design. To illustrate these angles, FIG. 1B includes a first side line 17 and a second side line 19.

The first side line 17 contacts the two outermost points of the first side 13 of the device (i.e., the line is tangent to the two outermost points of the first side 13) and extends at least from the distal end 6 of the handle 12 past the proximal end 8 of the handle. The first side line 17 has been extended on FIG. 1B for clarity. The angle $\phi_1$ between the first side line 17 and the line 15 along the skin contacting surface 16 can be about 135° or less, for instance from about 30° to about 90°, or from about 45° to about 85°. Note that this angle is as measured through the device from the skin contacting surface 16 of the device to the first side 13 of the device, i.e., the angle passes within the structure of the device 10.

The second side line 19 contacts the two outmost points of the second side 11 of the device and extends at least from the proximal end 8 of the handle 12 to the distal end 6 of the handle 12. The second side line 19 has been extended on FIG. 1B for clarity. The angle $\phi_2$ between the second side line 19 and the line 15 of the skin contacting surface can be about 90° or greater, for instance from about 90° to about 135', or from about 95° to about 120°. Note that this angle is also measured from the skin contacting surface 16 of the device to the second side 11 of the device, i.e., as measured within the structure of the device.

In general, the two angles $\phi_1$ and $\phi_2$ will not add to 180° and in one embodiment will add to less than 180°. In other words, the two sides 13 and 11 will not be parallel to one another. This allows for each side to be ergonomically designed for diagnostic and procedural applications independently of one another, and insures that the device can be comfortably and stably held for both types of applications.

An ultrasound system can include a detector that can register the location of a target that is associated with a subdermal device. This information can be electronically communicated to a processor and processed with input data (e.g., the length of the needle, etc.) and displayed as a real time image of a virtual needle in conjunction with a sonogram, i.e., the two images, the image developed from the data obtained by the detector, and the sonogram developed from the data obtained from the ultrasound transducer, can be displayed on the same monitor. Because the virtual needle location is correlated with the actual needle location, the location of the needle tip in relation to the subdermal site and the striking of the subdermal site by the needle tip can be seen in real time by an operator watching the virtual needle and the sonogram on the monitor during the procedure.

In general, any suitable detector can be utilized for detecting the target. For instance, a detector can utilize infrared (IR), ultrasound, optical, laser, magnetic, proximity, or other detection mechanisms. In addition, the location of a detector is not critical, save that it is capable of detecting the target that is associated with the subdermal device during use. In addition, the target can be any suitable item. It can be all or a portion of the subdermal device itself, or can be directly or indirectly attached to the subdermal device.

In one embodiment, the detector can be a permanent component of a device. For instance, the ultrasound device 10 can include a series of sensors (not shown) within the handle 12 that form a detector along a length of second side 11. The sensors can detect the presence and/or motion of a target that can be attachable to a subdermal device. In one embodiment of a magnetic based detection system, sensors can be Hall effect sensors that are sensitive to a magnetic field and the target can include one or more magnets. One exemplary embodiment of a magnetic based detection system as may be incorporated in a device is describe in U.S. Pat. No. 8,425,425 to Hagy, et al., previously incorporated herein by reference. Other magnetic-based sensor systems can include, without limitation, anisotropic magnetoresistive sensors, tunneling magnetoresistive sensors, etc.

The detector is not necessarily included within the handle 12 of the device, and can optionally be either permanently or removably attached to the handle 12, the base 14, or any other portion of a system. For instance, in one embodiment, a detector can be located on a sterilizable shield, discussed in more detail below.

Referring again to FIG. 1, the device 10 can include a cable 9 that can extend from the handle 12 of the device and carry power supply lines, information lines, etc. to provide communication from the device to other components of a system. The device 10 can also include a connector 5 and a connector 3 that can be used to connect the device 10 to another component of the system (e.g., a sterilizable shield, a needle guide, a component of a guidance system, etc.), for instance to properly align the ultrasound transducer with a subdermal device during use. Of course, any style of connector can be utilized, and a system can include one, two, three or more connectors to combine components of a system to one another.

Ultrasound device 10 also includes guide rails 43, 45 (described further herein) that can be components of a guidance system and used to guide a subdermal device during insertion and improve targeting of the subdermal device to an internal target.

FIG. 2 illustrates one embodiment of a sterilizable shield 20. In this illustrated embodiment, the shield 20 has a shape to be utilized in conjunction with the device 10 of FIG. 1, for instance in procedural applications requiring a sterile field. Of course, the shape of a sterilizable shield can vary as needed to fit a particular ultrasound device. FIG. 2 includes a perspective view (FIG. 2A), a side view (FIG. 2B) and a front view (FIG. 2C) of the sterilizable shield 20. A sterilizable shield 20 can be formed of sterilizable materials as are generally known in the art. In one embodiment, a sterilizable shield 20 can be formed of single-use materials such as polymeric materials, and the entire shield can be properly disposed of following a single use. In another embodiment, a sterilizable shield 20 can be utilized multiple times, in which case it can be formed of a material that can be properly sterilized between uses. A sterilizable shield 20 can be formed of a moldable thermoplastic or thermoset polymeric material (or combinations thereof) including, without limitation, polystyrenes, polyolefins (e.g., polyethylene, polypropylene), polyurethanes, polysiloxanes, polymethylpentene (TPX), polyester, polyvinyl chloride, polycarbonate, and so forth. The shield can include materials of different characteristics, such as materials of different stiffness, elasticity, strength, etc. For instance, a combination of stiff and pliable materials can be utilized in forming a sterilizable shield.

Sterilizable shield 20 can include a shield base 22, a coupling 24, a casing 26, and a drape 21 (included in FIG. 2A). The shield base 22 can be formed of an ultrasonic transmissive material. Shield base 22 can be of any suitable size and shape, and can be formed such that the base of an ultrasound device may be seated firmly in shield base 22. For instance, the connector 5 of the ultrasound transducer 10 can align with and connect to a mated connector 25 and the connector 3 of the ultrasound transducer 10 can align with and connect to a mated alignment coupling 38. In this particular embodiment, the alignment coupling 38 is a component of a needle guide base 37 that fits into a connection port 23 on the shield base 22 as shown in FIG. 2. Generally, a small amount of an ultrasonic gel can be placed between the skin contacting surface 16 of the ultrasound device 10 and the interior of the shield base 22 during seating to prevent any air between the two and promote transmission of ultrasonic waves.

Coupling 24 can connect the shield base 22 to the casing 26. The casing can extend to cover at least a portion of the ultrasound device 10. For instance, in the illustrated embodiment, the casing 26 is formed of a non-pliable material that can extend upward from the base and enclose at least a portion of an ultrasound device that can be seated in the shield base 22. As shown in FIG. 2A, the casing 26 can be attached to a drape 21 that can cover an additional amount of the ultrasound device. Any combination of components can be utilized in forming a sterilizable shield. For instance, in another embodiment, the sterilizable shield can include a pliable drape directly connected to the shield base. The pliable drape can be formed of any suitable pliable material, for instance a pliable polymeric material such as a pliable sheet or film that can enclose the top of the ultrasound device with only the cable 9 extending out of the sterilizable shield.

The utilization of a separate coupling 24 is not a requirement, and in other embodiments the shield base 22 and the casing 26 (or drape 21) can be of either a unitary construction or alternatively directly connected to one another without the need for a separate coupling that attaches the two together.

FIG. 3 illustrates another embodiment of a system that can include a pliable, single-piece sterilizable shield 320 that can cover all or a portion of an ultrasound device 310. The sterilizable shield 320 can be pliable but still have a shape that is similar to that of the ultrasound base and/or can be somewhat elastic in nature in order that the sterilizable shield 320 can extend over the base 314 of the ultrasound device 310 so as to securely wrap at least the base 314 of the device 310 without interfering with the workings of the system.

The system of FIG. 3 also includes a shell 350 that can include a shell base 351 and an arm 352 that extends from the base 351. The shell base 351 can fit over the base 314 of the ultrasound device and can help to hold the sterilizable shield 320 in place. In addition, the shell base 351 can be open at the bottom such that upon assembly (FIG. 3B) the contacting surface 316 of the ultrasound device 310 wrapped by the sterilizable shield 320 can be placed against the skin of a patient with material of the shield 320 between the contacting surface 316 and the patient's skin and none of the shell there between. The shell base 351 can be directly or indirectly attached to the base 314 of the ultrasound device 310 by one or more connections with the sterilizable shield 320 between the two or can be simply friction fit against the base 314 with the sterilizable shield between the two. For instance, the system can include connection point(s) at the arm 352 of the shell 350 and/or at the base 351 of the shell 350.

The arm 352 can extend from the base 351 such that upon assembly with an ultrasound device 310, the arm 352 extends along a length of the ultrasound device 310. The arm 351 can be a component of a needle guidance system that can serve to stabilize and target a subdermal device (e.g., a needle, as shown in FIG. 3) as it is directed to a target. In one embodiment, the arm 352 can carry a needle guide (or one or more components of a needle guide system) and can also carry a detector for detecting the motion of the needle as it passes along the arm 352 and into the patient. In another embodiment, a detector can be located in the ultrasound device and the arm 352 can carry a needle guide (or one or more components of a needle guide system).

FIG. 4 illustrates one embodiment of a needle guide system 30. The needle guide system 30 is an ambidextrous system that can efficiently hold and guide a needle (or other subdermal device) during targeting and can also open on either side to release the needle from the needle guide system following targeting.

In one embodiment, an ambidextrous needle guide system can include components for proper alignment with the transducer of an ultrasound device. For instance, referring to FIG. 2, the connection port 23 can be utilized for connection and alignment between a needle guide system 30 and an ultrasound device via alignment coupling 38 of the system 30. The needle guide system 30 includes a base 37, and the base 37 includes an alignment coupling 38. Upon attachment of the needle guide base 37 to a sterilizable shield (or to a shell that is used in conjunction with a sterilizable shield) via a suitable connection port (such as connection port 23), the alignment coupling 38 can also properly align the guidance system 30 with the ultrasound transducer. For instance, when the ultrasound transducer 10 is properly seated in the base 22 of the sterilizable shield 20, the alignment coupling 38 and connector 3 can mate and properly align the needle guide with the ultrasound transducer.

Of course, a device can include no alignment coupling or more than one alignment coupling, and these can be of the same or different shapes as one another. The utilization of one or more features that incorporates components so as to connect a needle guidance system with a sterilizable shield and/or to properly align the needle guidance system with the ultrasound transducer can insure proper alignment between the needle guide and the ultrasound transducer during a procedural application.

In any case, the needle guide base 37 can be permanently or removably attached to a sterilizable shield such that when an ultrasound device is assembled with the sterilizable shield, a subdermal device that is passed through the needle guidance system 30 will be aligned with the ultrasonic beam emitted from the transducer of the device and subdermal device can be accurately targeted to an internal site.

The needle guidance system 30 can include separable hinges 33, 35 that can allow for separation of the needle guidance system (as well as the ultrasound device and the sterilizable shield) from the needle following placement of the needle within the subject. Following proper placement of the needle at an internal site, the needle can be held within the subject and the needle guidance system 30 can be removed from around the needle so as to allow further procedural steps such as threading of a guide wire through the needle and into the subject's blood vessel.

In the illustrated embodiment of FIG. 4, the needle guidance system can be ambidextrous such that separation from a needle can be carried out quickly and easily by an operator using either the thumb or finger of either the left or right hand to control the device, FIGS. 4, 5 and 6 illustrate one embodiment of an ambidextrous needle guidance system 30.

The system 30 includes a base 37. The base can be removably attachable to a sterilizable shield or some other component of an ultrasound device system. Alternatively, the base can be formed as a permanent fixture of a shield or some other component (e.g., a shell) of a system. In one embodiment, the needle guide base 37 can be designed such that it can be attached and removed multiple times from another component such as a sterilizable shield. This is not a requirement, however, and in other embodiments the needle guide base 37 can be permanently disabled (e.g., snapped or broken) following a single use.

Figure 4D:
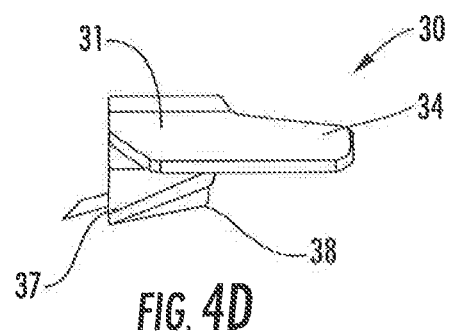
Figure 5A:
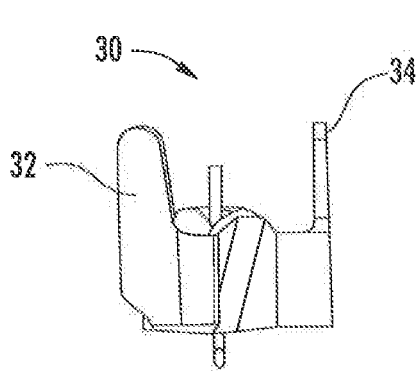
FIG. 5 illustrates the ambidextrous needle guide of FIG. 4 in an open configuration following opening from the first side of the guide including a front view (FIG. 5A), a top view (FIG. 5B), a perspective view (FIG. 5C), and a side view (FIG. 5D).
Figure 5C:
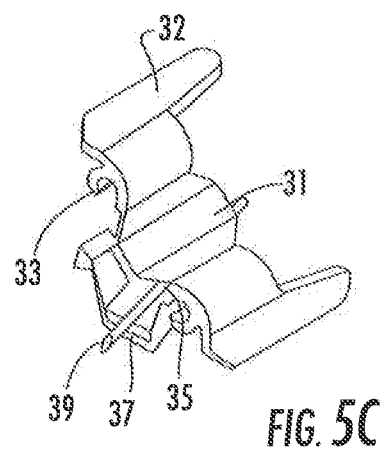
Figure 5B:
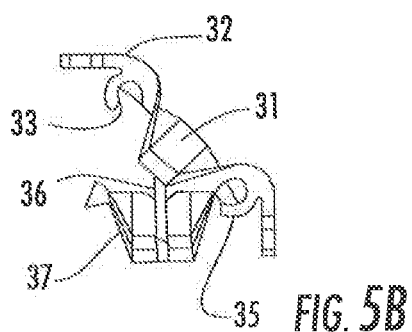
Figure 5D:
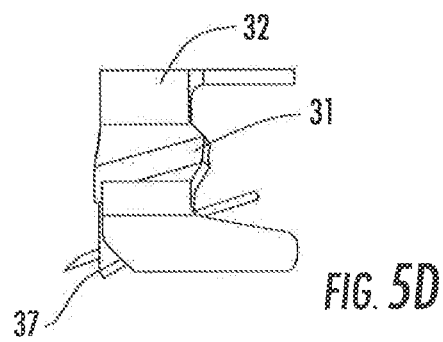

FIG. 4 illustrates an ambidextrous needle guidance system 30 in a closed configuration including a front view (FIG. 4A), a top view (FIG. 4B), a perspective view (FIG. 4C), and a side view (FIG. 4D). The system 30 includes a rotatable member 31 and a base 37 with a passage 36 defined between the two when the two are assembled together to form the closed assembly. The passage 36 can pass from one side to the other (e.g., from the top to the bottom) of the closed assembly and can generally be sized so as to allow a particular gauge needle. The base 37 can include the alignment coupling 38 on one side of the base. The passage 36 is of a size to allow a subdermal device such as a needle 39 to freely pass through from the top of the assembly to the bottom, as shown in FIG. 4A. The rotatable member 31 includes a first tab 32 and a first separable hinge 33 on a first side of the needle guide 30 and a second tab 34 and a second separable hinge 35 on a second side of the device. During use, the rotatable member 31 can be opened on either side and separated from the base 37 on the open side so as to release a needle 39 held in the passage 36. More specifically, the rotatable member 31 can be opened at either the first side or the second side by use of either the first tab 32 or the second tab 34, depending upon whether the operator is using their finger, their thumb, their left hand, or their right hand.

FIG. 5 illustrates the needle guidance system 30 in an open configuration following opening of the passage 36 from the first side. FIG. 5 includes a front view (FIG. 5A), a top view (FIG. 5B), a perspective view (FIG. 5C), and a side view (FIG. 5D). As can be seen, when the first tab 32 is pushed to an open configuration, the first separable hinge 33 releases and the rotatable member 31 rotates about the second hinge 35 on the second side. Thus, the needle guide 30 opens at the first side and remains closed at the second side.

FIG. 6 illustrates the needle guidance system 30 in an open configuration following opening of the passage 36 from the second side. FIG. 6 includes a front view (FIG. 6A), a top view (FIG. 6B), a perspective view (FIG. 6C), and a side view (FIG. 6D). As can be seen, when the second tab 34 is pushed to an open configuration, the second separable hinge 35 releases and the rotatable member 31 rotates about the first hinge 33 on the first side. In this embodiment, the needle guide 30 opens at the second side and remains closed at the first side.

The hinges 33, 35 can be of a design and material (e.g., a polymeric material) such that they can be released relatively easily, with a forward push by the thumb or forefinger of an operator. Thus, the needle guidance system 30 can be opened and the needle released by either the left or right hand of an operator, as desired. This can improve stability of the device during needle release as an operator need not undergo any awkward contortions to release the needle, which can help to prevent dislodgement of the needle during the procedure.

FIG. 7 and FIG. 8 present two perspective exploded views of a system including an ultrasound device 10 as illustrated in FIG. 1, a sterilizable shield 20 as illustrated in FIG. 2, a needle guidance system 30 as illustrated in FIG. 4, and a needle 39, as an example of a subdermal device system incorporating the guidance system. As can be seen, the sterilizable shield can be assembled to include the shield base 22, the coupling 24, the casing 26, and the drape 21. The ultrasound device can be seated within the sterilizable shield and held firmly in place by use of the mating of connector 5 and the mated connector member 25 as well as by the connector 3 and the alignment coupling 38 that mate via the connection port 23.

The base 37 of the needle guide can be attached to the base 22 of the sterilizable shield by use of the connection port 23, as shown, and the rotatable member 31 of the needle guide can be attached to the base 37 of the needle guide via the first hinge 33 and the second hinge 35.

In this particular embodiment, the needle 39 is associated with a target 48, e.g., a magnetic target, which can be detected by a detector in the ultrasound device, as discussed previously. For instance, the detector can include a series of Hall effect sensors located along the length of the handle 12 and on the second side 11 of the ultrasound device 10. As shown in FIG. 8, in this embodiment, the second side 11 can include ridges 43, 45 that can help to guide the target 48 that is associated with the needle 39 as the needle 39 passes through the needle guide 30. Such guidance features can be a component of the ultrasound device as illustrated in FIG. 8 or alternatively can be a component of another member of the device. For instance, when utilizing a sterilizable shield system as illustrated in FIG. 3, guidance features can be formed on the shell 352 and help to guide the needle as it passes through the guidance system.

In the embodiment of FIG. 8, the sensors can be arranged in one or more rows extending lengthwise along the second side 11 of the ultrasound device 10. As is known, the presence of a magnetic field can induce a voltage in a Hall effect sensor that is proportional to the size of the magnetic field. The voltage of each sensor can be electronically scanned and processed to determine the location of the target 48 relative to the sensing array (i.e., the detector). Processing can include grouping the sensors and providing their outputs to a series of multiplexers which, in turn, are connected to a processor including software for analyzing the outputs and determining the location of the target 48 with regard to the entire sensor array. As the distance from the target 48 to the tip of the needle 46 is constant and known, the processor can likewise compute the location of the tip of the needle 46.

The processing of the sensor outputs can include determining which sensor has the highest (or lowest, depending upon the magnetic field orientation) voltage output in a recognized grouping, corresponding to the location of the target 48. In one embodiment, a processor can analyze the output of the sensor having the highest voltage output and a predetermined number of sensor(s) to each side. The analog outputs of the sensors can be converted to digital output according to known methodology that can then be evaluated to determine the target location. More details concerning suitable magnet assemblies are described in U.S. Pat. Nos. 5,285,154 to Burreson, et al. and U.S. Pat. No. 5,351,004 to Daniels, et al., both of which are incorporated herein by reference.

In one embodiment, the subdermal device or the system that incorporates the subdermal device can include one or more tags that can carry information about the subdermal device and/or the subdermal device assembly including, without limitation, the device type (e.g., needle, biopsy device, etc.) as well as the device geometry such as gauge, length, cross section, etc. The information from the tag(s) can be utilized to accurately determine a characteristic distance of the subdermal device assembly, for instance the distance from the center of the target 48 to the tip of the needle 46, which can then be used to accurately correlate the location of the needle tip 46 as determined by the detection system with the actual location of the needle tip in the subdermal environment.

In one embodiment, the tag can include an identifying reference (e.g., a single number identifying the subdermal device), for instance in the form of an information chip. This reference can then be transmitted a processor that can be preprogrammed to recognize the code and access the preprogrammed information needed for identifying the characteristics of the needle 39. Alternatively, the tag can be designed to directly carry the desired information (e.g., geometric information).

The tag can be located at any convenient point on the subdermal device or an assembly including the subdermal device. For instance, the tag may be located on or in a needle hub or attached to a needle hub, or may be a component of the target 48 (e.g., a magnet or magnets) or may be located on a needle guide, a shell, or a sterilizable shield. For instance, the subdermal device assembly can include a stylet, a syringe, a multi-component hub, a butterfly grip, and so forth, and the tag may be located on or in or attached to any component of the assembly.

The tag can use any of a variety of technologies to provide information to a processor of the ultrasound system. In one embodiment, the tag can be a radio-frequency identification (RFID) tag. An RFID tag can be a passive type or an active type of RFID tag as is known in the art. By way of example, RFID tags as described in U.S. Pat. Nos. 8,174,368 to Usami, U.S. Pat. No. 8,035,522 to Oroku, et al., U.S. Pat. No. 8,325,047 to Marur, et al., and U.S. Pat. No. 7,876,228 to Kroll, et al., all of which are incorporated herein by reference, can be utilized in the probe detection system.

While the general construction shown in FIG. 7 and FIG. 8 can be used, it should not be considered to be limiting. In this particular embodiment, the target 48 incorporates a permanent magnet, with a magnetic field having a flux density which has a maximum at or adjacent to the center of the magnet and which decreases as a function of the distance moved away from the magnet. A single thin magnet can be used, or an array of magnets located side by side. The magnet or array of magnets then can be mounted in conjunction with a needle 39. Moreover, and as discussed previously, the system need not include a detector at all and, when included can incorporate any suitable detection system. Additionally, when included the detector can be located at any suitable location within the system. For instance, the detector may be located on the sterilizable shield, rather than within or on the ultrasound device.

In those embodiments in which a magnetic detection mechanism is utilized, the magnetic material of the target 48 can be any suitable permanent or electro-magnetic material that has a high enough energy to be detectable over the distance between the target 48 and the sensors. A non-limiting list of suitable materials can include, without limitation, samarium cobalt, neodymium, or iron boron.

Figure 9:
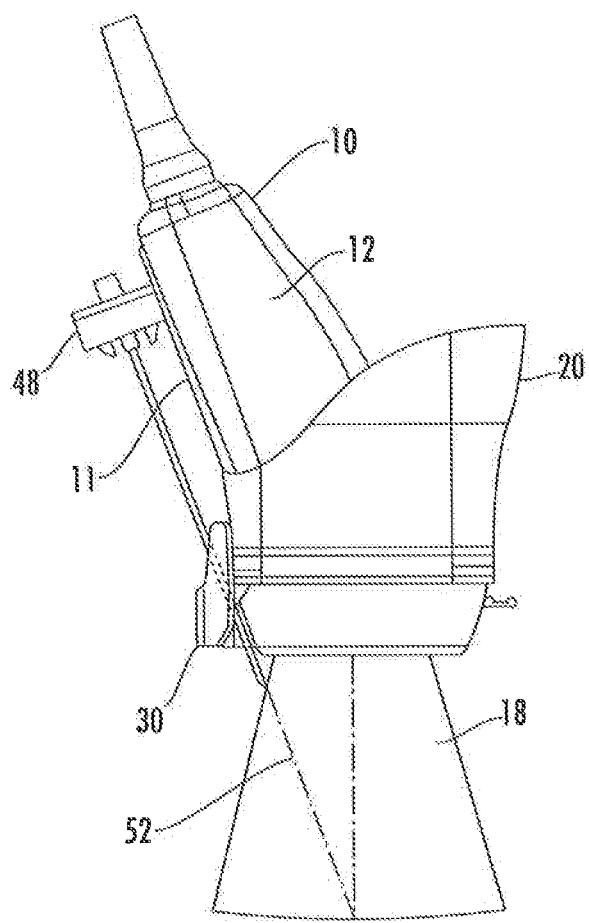
FIG. 9 illustrates a side view of the system of FIG. 7 following assembly.
Figure 10:
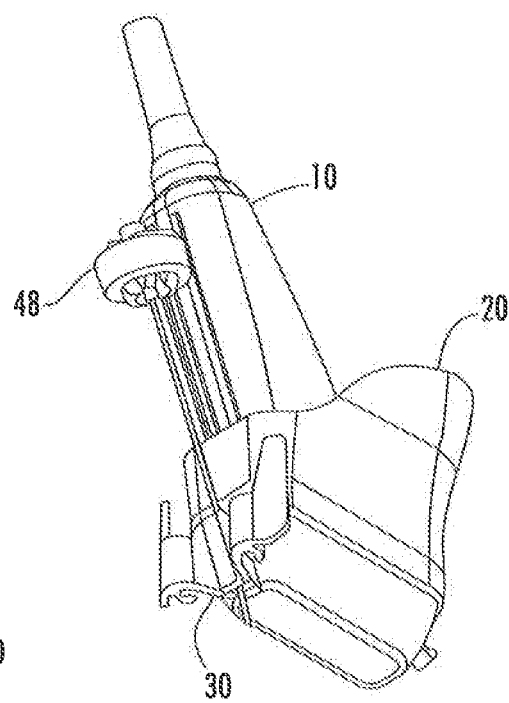
FIG. 10 illustrates a perspective view of the system of FIG. 7 following assembly.
Figure 11:
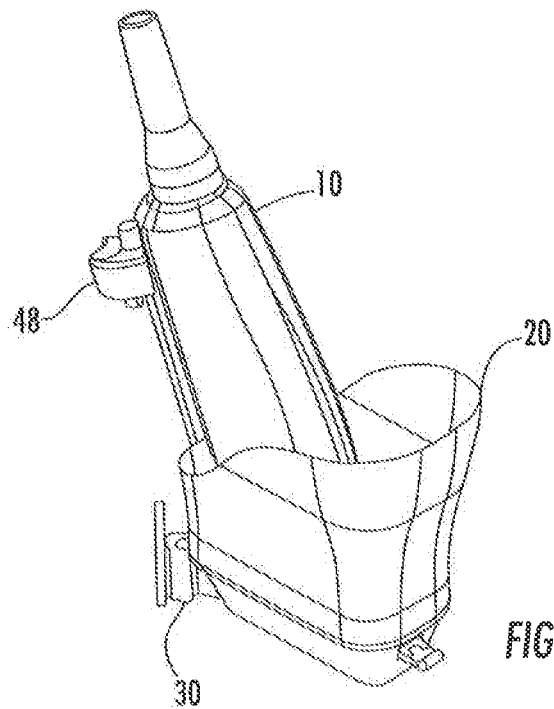
FIG. 11 illustrates another perspective view of the system of FIG. 7 following assembly.

FIG. 9, FIG. 10, and FIG. 11 present a side view, a first perspective view, and a second perspective view of the system of FIG. 7 and FIG. 8 following assembly of the ultrasound device 10 with the sterilizable shield 20 (the drape 21 has been excluded from these views for clarity) and the needle guide 30. As shown in FIG. 9, the emitted ultrasonic wave 18 can align with the needle path 52. The target 48 can pass along the second side 11 of the handle 12 and the detector within the handle 12 can recognize the target 48 and determine the location of the target 48 in relation to the detector.

Signals from the sensors can create a data stream which can be sent to a processor. A processing unit can be internal or external to an ultrasound device 10. For example, data from sensors can be sent to a standard lap top or desk top computer processor or part of a self-contained ultrasound system as is known in the art. A processor can be loaded with suitable recognition and analysis software and can receive and analyze the stream of data from sensors. Input data for the processor, such as the length of the needle and so forth, can be entered into the processor by the user at the time of use or can be preprogrammed into the system as default data, depending upon the nature of the data. Through analysis of the data stream received from the detector, the processor can calculate the position of the needle tip relative to the ultrasound transducer, relative to a sensor, relative to the skin contacting surface of the device, or relative to any other convenient reference point. The processor can communicate this position information digitally to a monitor and the information can be displayed on the monitor such as in a numerical format or as a real time image of a virtual needle.

A processing unit can also include standard imaging software as is generally known in the art to receive data from the ultrasound transducer that is a part of the ultrasound device 10. More specifically, the processor can receive data from the ultrasound transducer concerning the reflection of the emitted ultrasonic wave. This data can be processed according to known methodology to form a sonogram on a monitor. The position information concerning the position of the needle can be displayed on the monitor in conjunction with, e.g., overlaid on, the sonogram that displays an image of the subdermal site, such as a blood vessel.

In such a manner, an ultrasound system can be utilized to show the approach of a subdermal device toward a targeted site on a monitor throughout the entire procedure. In addition, the system can be utilized to ensure the device tip remains at the subdermal site during subsequent procedures. For example, as long as the detector is interacting with the target the virtual image of the needle can remain on the monitor. Thus, any motion of the needle tip in relation to the subdermal site can be noted by an observer.

As previously mentioned, the ergonomic devices can be held in different orientations depending upon which mode of operation is being carried out. As shown in FIG. 12, an ultrasound device 10 can be utilized in a diagnostic application, in which case the device need not necessarily be contained in a sterilizable shield. In this embodiment, the user can grasp the device from the side 11 and the side 13 can be considered to be the 'front' of the device during the diagnostic application. FIG. 12A illustrates a front view of the orientation of the ultrasound device 10 during a diagnostic application and FIG. 12B illustrates a side view of the orientation of the ultrasound device during a diagnostic application. Of course, the orientation of the device during a procedure can be altered for comfort or convenience, and the orientation of the device will not affect the ability of the device to carry out the desired functions.

The orientation of the device 10 can differ during a procedural application. For instance, in the embodiment as illustrated in FIG. 13, the device 10 can be combined with a sterilizable shield 20 and a needle guidance system 30. FIG. 13A illustrates a front view of the orientation of the ultrasound device 10 and system during a procedural application and FIG. 13B illustrates a side view of the orientation of the ultrasound device and system during a procedural application. The device can be oriented such that a user can grasp the device from the side 13 and the side 11 can be considered to be the 'front' of the device during the procedural application. In this orientation, the user can exert good control and skin contact during the application and can easily access the subdermal device and the rotatable member 31 of the needle guide with either their forefinger or their thumb, depending upon which approach is more comfortable for the user. Moreover, though shown as being grasped in a left hand, the device would be equally comfortable and the components of the device would be equally accessible if the user were to grasp the device with the right hand.

Figure 14A:
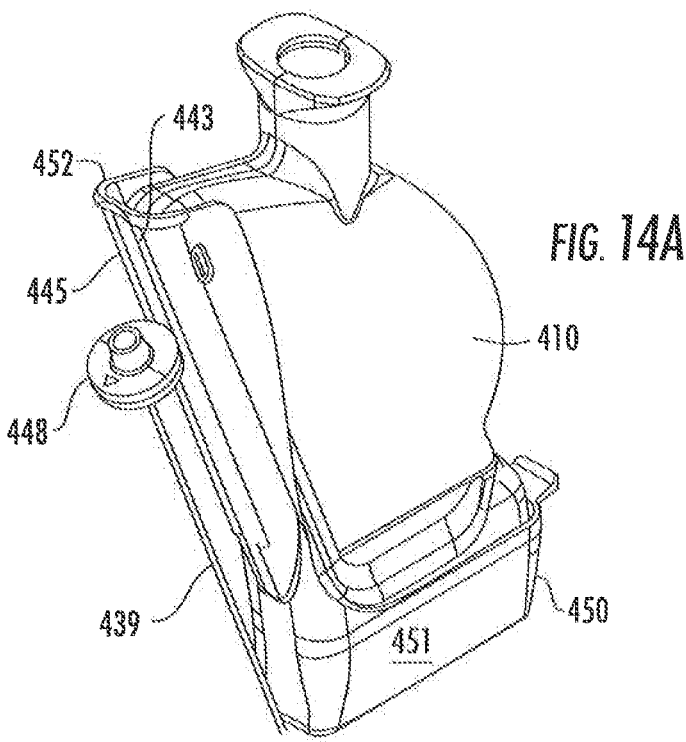
FIG. 14 illustrates a guidance system for an ultrasound device including a perspective view (FIG. 14A) of an ultrasound device seated in the system and a sectional view (FIG. 14B) of the system along the section A-A as shown in FIG. 14C.
Figure 14C:
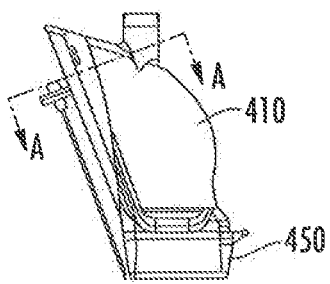
Figure 14B:
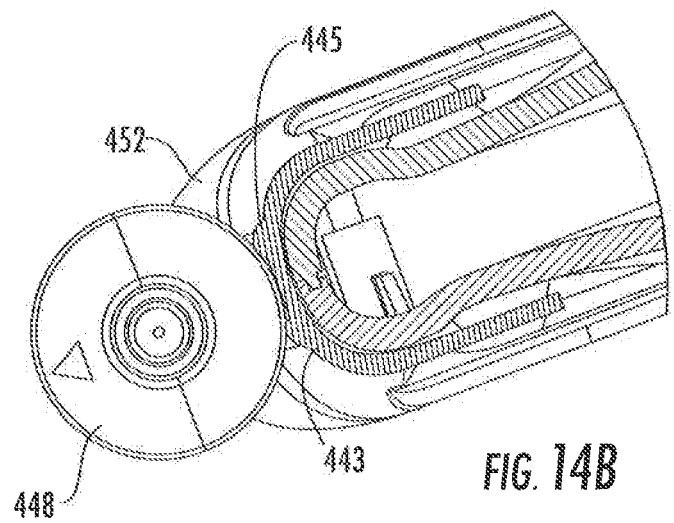

As previously mentioned, the guidance system can include guide rails on the transducer housing, the sterilizable shield, the shell, or some other component of the system that can help to guide the subdermal device to the internal target. As illustrated in FIG. 8, the guide rails 43, 45 can be relatively simple extensions from the adjacent surface that form a track that can constrain and help to guide the target 48. FIG. 14 illustrates a similar track-based guidance system in which the ultrasound device 410 can be seated in a shell 450 that includes a base 451 and an arm 452. The shell 450 can be utilized alone with the ultrasound device 410 or alternatively in conjunction with a sterilizable shield such as a pliable sock-type shield that covers a least a portion of the ultrasound device 410. The arm 452 can include guide rails 443, 445 that can contact the target 448 and constrain motion of the target in the lateral direction and help to guide the subdermal device 439 as it is targeted to an internal target. FIG. 14A illustrates the system in a perspective view, and FIG. 14B illustrates a sectional view along the section A-A as shown in FIG. 14C. As shown in FIG. 14B, the guide rails 443, 445 rest against the target 448 (or a member that is attached to or contains the target). Thus, as the needle 439 is advanced, the guide rails 443, 445 will help to track the needle 439 correctly.

The guide rails 443, 445 can extend along the length of the arm or only partly along the length, as desired. In addition to one or more guide rails, a guidance system can include a needle guide portion that can grasp the needle as it advances and hold the needle and/or target at the desired alignment. For example, the shell 450 and guide rails 443, 445 can be used in conjunction with the ambidextrous system of FIG. 4 to provide guidance for a subdermal device, though any other suitable needle guide can alternatively be utilized.

Figure 15:
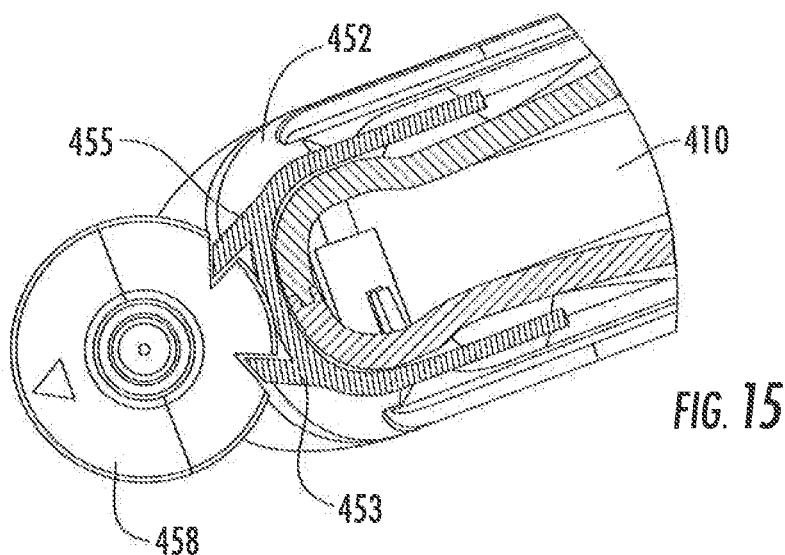
FIG. 15 illustrates a sectional view of an interlocking guidance system.

A track-based guide rail system can be of any shape, size and level of interaction with the subdermal device. For instance, FIG. 15 illustrates a sectional view of a guidance system in which the guide rails 453, 455 of the shell arm 452 interlock with the target 458 to more tightly hold the target 458 against the shell 452 and in proper relationship with the ultrasound device 410 during use. Though illustrated as interlocking with the target itself in FIG. 15, guide rails of such as system can interlock with or otherwise constrain any suitable component of the subdermal device or a member associated with the subdermal device. For example, a target (e.g., a magnet) for a detection system can be held by or formed within another member that in turn can be formed to interlock with the guide rails.

Figure 16:
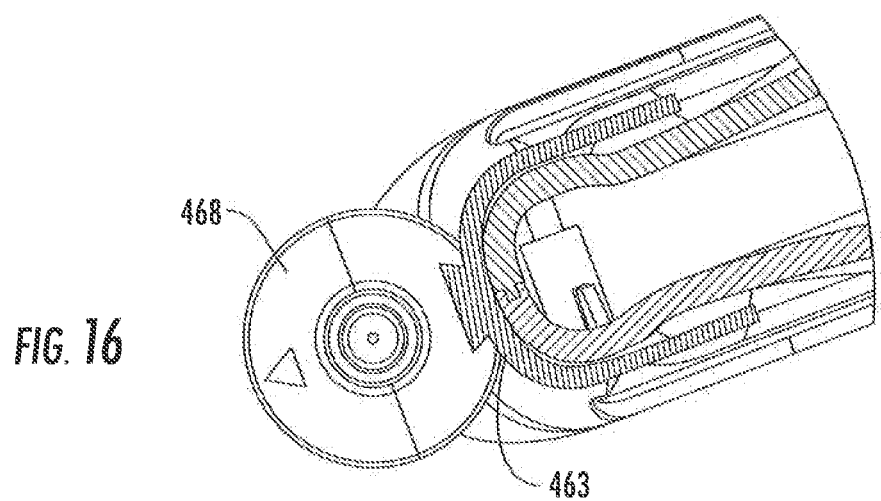
FIG. 16 illustrates a sectional view of another interlocking guidance system.
Figure 17:
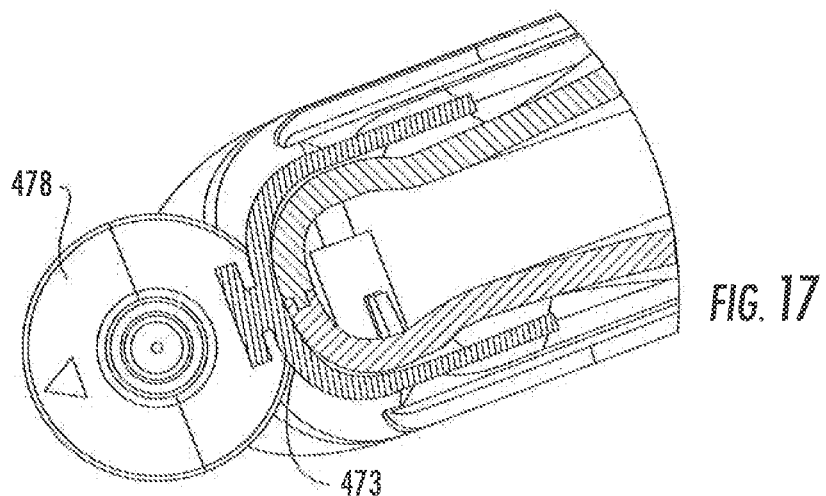
FIG. 17 illustrates a sectional view of another interlocking guidance system.

A track-based guidance system can include one, two, three or more guide rails as desired to form a track for improved targeting of a subdermal device. For example, FIG. 16 and FIG. 17 illustrate two embodiments that incorporate a single guide rail 463, 473 respectively. In FIG. 16, the guide rail 463 can interlock with the target 468 with dove-tail type geometry so as to grasp the target 468 while still allowing the target to move axially during insertion of the subdermal device. FIG. 17 illustrates a T-shaped guide rail 473 that interlocks with the target 478. Any shape or size of guide rail is encompassed herein. For instance, a dove-tail type of interlock can be a positive or negative dove-tail.

Figure 18A:
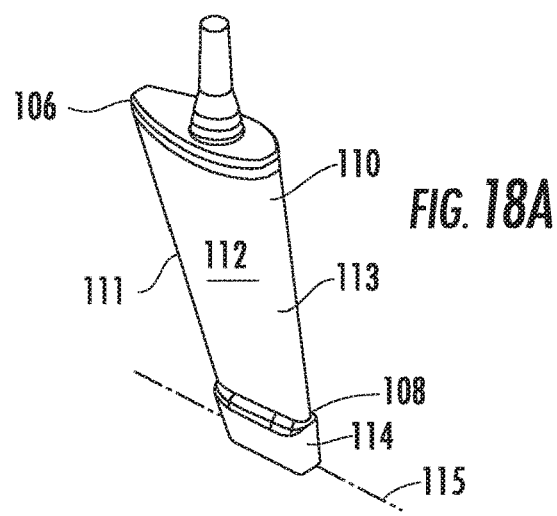
FIG. 18 illustrates another embodiment of an ultrasound device including a perspective view (FIG. 18A), a side view (FIG. 18B), and a front view (FIG. 18C).
Figure 18B:
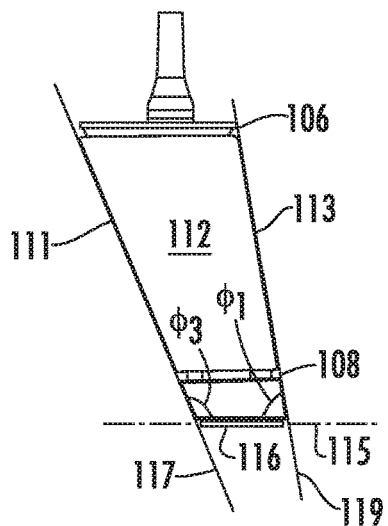
Figure 18C:
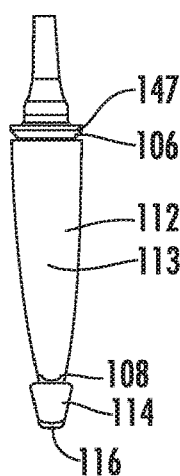

The ultrasound devices and shields that incorporate the disclosed guidance systems are not limited to any particular geometry. For instance, FIG. 18 illustrates another embodiment of an ergonomic ultrasound device 110 including a perspective view (FIG. 18A), a side view (FIG. 18B), and a front view (FIG. 18C). Device 110 includes a base 114, a handle 112, and a skin contacting surface 116. An ultrasound transducer can be contained within the base 114 and can emit an ultrasonic wave through the skin contacting surface 116 along a line 115, similar to that of the device 10 illustrated in FIG. 1.

The handle 112 of the device 110 is set so as to be angled with the base 114 and can provide an ergonomic design for both procedural and diagnostic applications. In general, the angles of the handle to the base will not be the same on the first and second sides 113, 111 of the device. To illustrate these angles, FIG. 18B includes a first side line 117 and a second side line 119.

The first side line 117 contacts the two outermost points of the first side 113 of the device and extends from at least the proximal end 108 of the handle 112 to the distal end 106 of the handle along the first side 111. Note that in this particular embodiment, the first side 113 is essentially straight hence the first side line 117 runs generally coincident with the first side 113. The first side line 117 has been extended on FIG. 18B for clarity. The angle $\phi_3$ between the first side line 117 and the line 115 of the skin contacting surface can be greater than 90°, for instance from about 92° to about 135°, or from about 95° to about 120°. Note that this angle is as measured from the skin contacting surface 116 of the device to the first side 111 of the device, i.e., as measured within the structure of the device 110.

The second side line 119 contacts the two outermost points of the second side 111 of the device and extends from the proximal end 108 of the handle 112 to the distal end 106 of the handle 112 along the second side 113 of the device 110. The second side line 119 has been extended on FIG. 18B for clarity. The angle $\phi_4$ between the second side line 119 and the line 115 of the skin contacting surface can be about 135° or less, for instance from about 30° to about 90°, or from about 45° to about 85°. Note that this angle is also measured from the skin contacting surface 116 of the device to the second side 113 of the device, i.e., as measured within the structure of the device.

In general, the two angles $\phi_3$ and $\phi_4$ will not add to 180°. In other words, the two sides 113 and 111 will not be parallel to one another. This allows for each side to be ergonomically designed for the diagnostic and procedural applications independently of one another, and insures that the device can be comfortably and stably held for both applications.

Figure 19A:
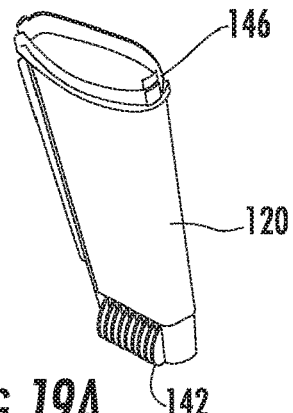
FIG. 19 illustrates a sterilizable shield for use with the device of FIG. 18 including a perspective view (FIG. 19A), a side view (FIG. 19B), and a front view (FIG. 19C).
Figure 19B:
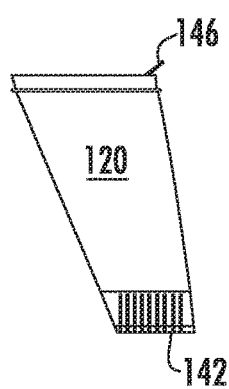
Figure 19C:
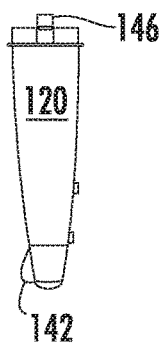

A sterilizable shield 120 as may be utilized in conjunction with the device 110 for procedural applications is illustrated in FIG. 19 including a perspective view FIG. 19A, a side view FIG. 19B, and a front view FIG. 19C. Sterilizable shield 120 is a single, monolithic shield within which the base 114 of device 110 can be seated. The sterilizable shield 120 can include a locking mechanism such as a tab 146 that can lock into a ridge 147 on the ultrasound device 110 to hold the ultrasound device 110 firmly in place within the sterilizable shield 120. Of course, a locking feature can be of any suitable design that can hold the components to one another as desired.

The sterilizable shield 120 can also include an extension 142 on the shield base 122. In this embodiment, the extension 142 is formed of a plurality of fins 143 that extend off of a side of the shield base 114. When present, the extension 142 may alternatively be formed of a single, monolithic piece. The extension 142 can help to stabilize the system when the shield 120 is held against a subject's skin.

Figure 20A:
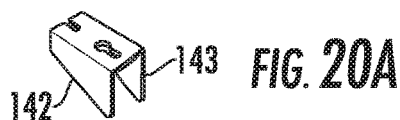
FIG. 20 illustrates an extension for use with the sterilizable shield of FIG. 19 including a perspective view (FIG. 20A), a side view (FIG. 20B) and a front view (FIG. 20C).
Figure 20B:
Figure 20C:

In one embodiment, a sterilizable shield 120 can include a removable extension 143 as illustrated in FIG. 20 in a perspective view (FIG. 20A), a side view (FIG. 20B), and a front view (FIG. 20C). The removable extension can be attached to a convenient location on the sterilizable shield 120, for instance via connector 145. The removable extension 143 can have an angled side 141 that can be held against a subject during use and stabilize the system.

The sterilizable shield of FIG. 19 can be utilized in conjunction with a guidance system for a subdermal device. For instance, FIG. 21 illustrates a first perspective view (FIG. 21A), a side view (FIG. 21B), a front view (FIG. 21C) and a second perspective view (FIG. 21D) of a system 210. The system 210 includes a sterilizable shield 220. The system 210 also includes an ambidextrous needle guidance system 230 as previously described. The ambidextrous needle guidance system 230 includes a rotatable member 231 and a base 237 with a passage 236 defined between the two for a needle 239. The passage 236 extends from the top of the assembly to the bottom of the assembly and allows for insertion of the needle 239 therethrough. A system 230 can also include a track-based guidance system as discussed above (not illustrated in FIG. 21) that can optionally form an interlock between the target 248 and the sterilizable shield 220 and can be used to enhance guidance of the subdermal device to a target.

A track-based guidance system can help to guide the subdermal device during insertion by utilization of one or more guide rails that can form a track along which the subdermal device can slide during insertion of the device tip into a patient's body. As discussed above, the guide rails can contact a component of the subdermal device so as to constrain the device within a track. The contact can be of any suitable level. For instance, the contact can be enough to constrain motion of the subdermal device in the lateral direction of the device and form a friction fit to hold the subdermal device and prevent free slippage in the longitudinal direction. Alternatively, a higher level of constraint can be created and the guide rail(s) can interlock with a component of subdermal device. For instance, the target of a detection system that is directly or indirectly associated with the subdermal device can be the component that is constrained by the guide rails. In one embodiment, the target of the detection system can be attached to (e.g., held by) or formed within another component that is not directly detected by the sensor and this component can contact the guide rail(s).

FIG. 22 illustrates another embodiment of components of a track-based guidance system. In this embodiment, the track-based guidance system can include a guide cartridge 130 that is illustrated in a perspective view (FIG. 22A), a front view (FIG. 22B), a side view (FIG. 22C) and a top view (FIG. 22D) in conjunction with a subdermal device including a needle 139 and a needle hub 132. The guide cartridge 130 can be sized to hold a hub 132 that can in turn connect with a needle 139 as illustrated or alternatively with some other subdermal device. For instance, the hub 132 can hold a biopsy device, an extraction device, a delivery vehicle, or any subdermal device. The track-based system can be universal with regard to subdermal device. For instance, the guide cartridge 130 can be sized to hold a standard needle hub 132 and any suitably sized and type of subdermal device can be attached to the hub and guided by use of the universal guide cartridge 130.

In those embodiments in which the system includes a detection system, the guide cartridge 130 and/or the hub 132 can carry the target for the motion detector and optionally also carry an information tag as previously discussed. For instance, as illustrated in FIG. 22B, the hub 132 can carry targets 488 in or on the hub such as permanent magnets the motion of which can be detected as the device is inserted into a patient. In another embodiment, the guide cartridge 130 can carry the target(s) for instance on a surface or within the body of the guide cartridge 130.

FIG. 23 includes FIG. 23A and FIG. 23B that illustrate two perspective exploded views of a system including the ultrasound device 110, the sterilizable shield 120, and guide cartridge 130 that contains a needle hub 132 connected to a needle 139, as well as a removable extension 143 and extensions 142. The system also includes a guide track 140 that can seat the guide cartridge 130 such that the guide cartridge 130 is interlocked with the guide track 140 and can slide along the guide track 140 as the needle 139 is inserted into a patient.

FIG. 24 illustrates this system following assembly in a perspective view (FIG. 24A), a side view (FIG. 24B), and a front view (FIG. 24C). The guide cartridge 130 is held within the guide track 140 is a slidable arrangement, for instance by friction fit of the guide cartridge 130 between the guide rails 182, 183 of the guide track. By sliding the guide cartridge 130 that holds the needle hub 132 down the guide track 140 the needle can intersect the wave plane 118 of the ultrasonic wave that is emitted from the ultrasound transducer 110 through the skin contacting surface 116 of the device 110. The ergonomic design of the ultrasound device 110 and the extensions 142, 143 of the sterilizable shield 120 can work together to provide a system that can be comfortably and stably held during a procedure.

As with other embodiments, the ergonomic device 110 and systems incorporating the device can be held in different orientations depending upon comfort of the use and which mode of operation is being carried out. By way of example, as shown in FIG. 25, the device can be utilized in a diagnostic application, in which case the device need not be contained in a sterilizable shield. In this embodiment, the user can grasp the device from the side 111 and the side 113 can be considered to be the 'front' of the device during the diagnostic application. FIG. 25A illustrates a front view of the orientation of the ultrasound device 110 during a diagnostic application and FIG. 25B illustrates a side view of the orientation of the ultrasound device 110 during a diagnostic application.

The orientation of the device 110 can differ during a procedural application. In this embodiment as illustrated in FIG. 26, the device 110 can be combined with the sterilizable shield 120 and a guidance system including a guide cartridge 130 and a guide track 140. FIG. 26A illustrates a front view of the orientation of the ultrasound device 110 during a procedural application and FIG. 26B illustrates a side view of the orientation of the ultrasound device during a procedural application. The device can be oriented such that a user can grasp the device from the side 113 and the side 111 can be considered to be the 'front' of the device during the procedural application. In this orientation, the user can exert good control and skin contact during the application and can easily access the needle hub 132, needle 139 and guide cartridge 130 with either their forefinger or their thumb, depending upon which approach is more comfortable for the user.

Figure 27A:
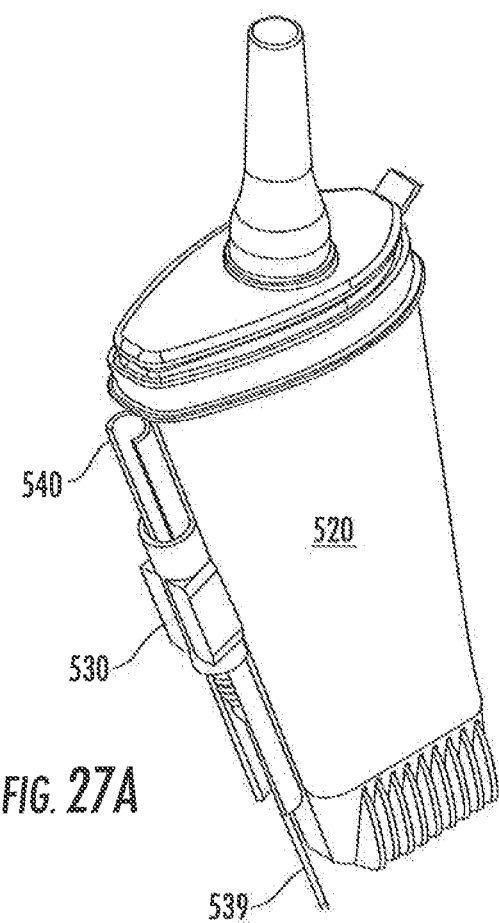
FIG. 27 illustrates an interlocking track-based guidance system including a perspective view (FIG. 27A) and a sectional view (FIG. 27B) along the section A-A as illustrated in FIG. 27C.
Figure 27C:
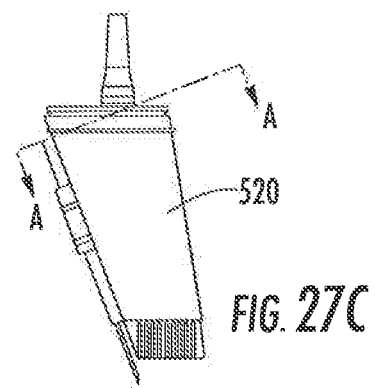
Figure 27B:
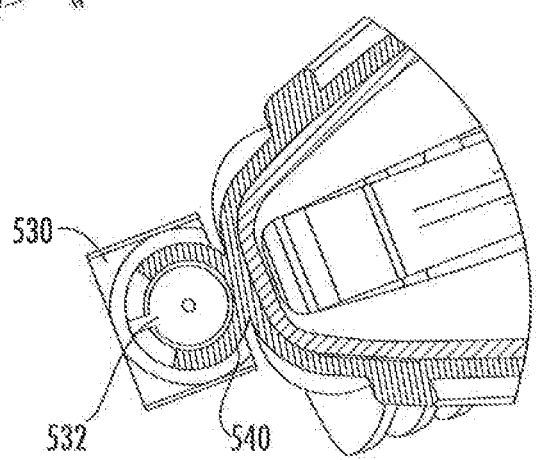

The orientation of a track-based guidance system can vary as can the nature of the interaction between the guide cartridge and the guide track. For instance, as illustrated in FIG. 27, the guide cartridge 530 can be oriented with respect to a sterilizable shield 520 at 90° as compared to the previous embodiment. FIG. 27 includes a perspective view (FIG. 27A) and a sectional view (FIG. 27B) along the section A-A as illustrated in FIG. 27C. As shown in the figures, the guide track 540 can securely hold the guide cartridge 530 via a partial circular guide rail that interlocks with the guide cartridge. The guide cartridge 530 can grasp the hub 532 that in turn is connected to the needle 539. Thus, by sliding the guide cartridge 130 down the guide track 540 the needle 539 can be inserted through the skin and to/into a target at a subdermal site.

Figure 28:
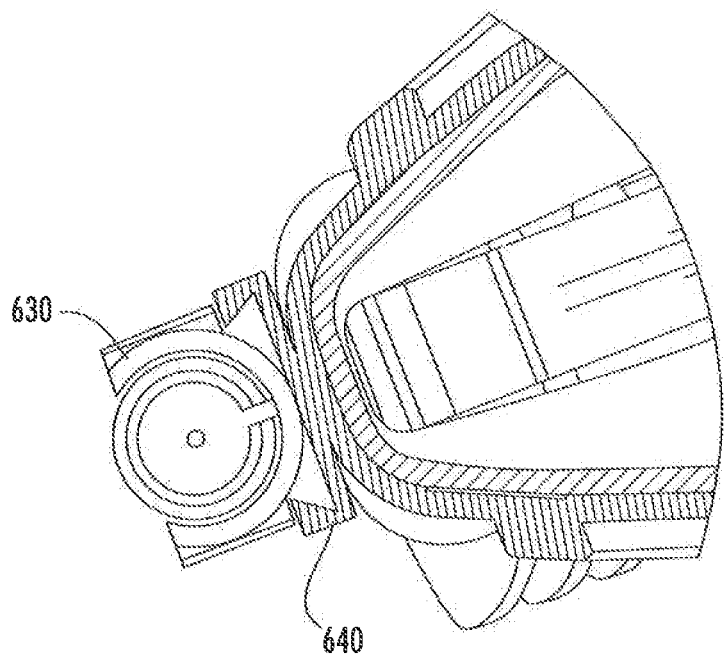
FIG. 28 illustrates a sectional view of another track-based guidance system.
Figure 29:
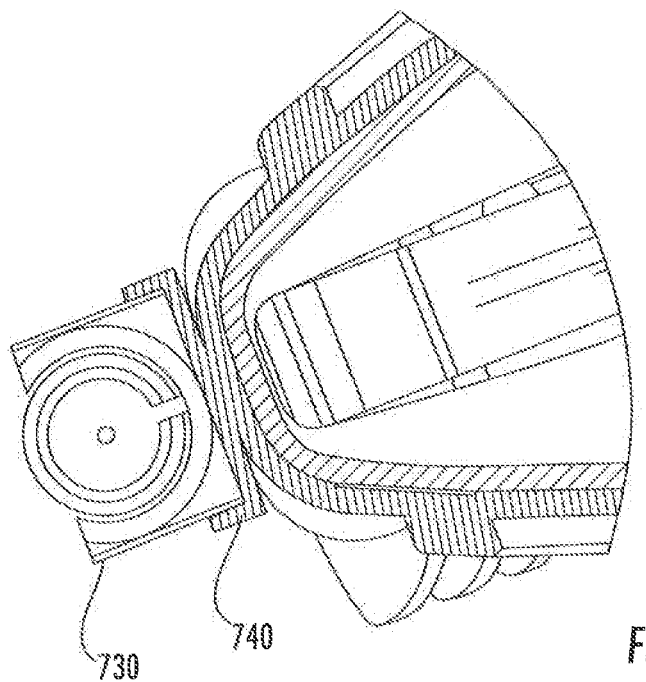
FIG. 29 illustrates a sectional view of another track-based guidance system.

FIG. 28 and FIG. 29 illustrate sectional views of alternative guide tracks 640, 740 respectively. As shown, the guide tracks 640, 740 can grasp and optionally interlock with the guide cartridge 630, 730 so as to hold the guide cartridge 630, 730 is slide down the guide track 640, 740 and the tip of the subdermal device that is held within the guide cartridge is delivered to the targeted internal site. As previously mentioned, the geometry of the guide rails is not limited, and alternative shapes are encompassed as would be understood by one of skill in the art.

The guide rail(s) that can form a guide track for a track-based guidance system can extend all the way down the device that carries the track or only part way, as discussed previously. In addition, in those embodiments in which there are multiple guide rails, the guide rails may be of different lengths. In those embodiments in which the guide rails end at a distance from the skin entry point for the subdermal device, it may be beneficial to include one or more additional guidance features for the needle. For instance, and as illustrated in FIG. 30, in one embodiment, a guidance system can include one or more guidance features 801, 802 that extend from a component of a system (e.g., an ultrasound device, a sterilizable seal, a shell, etc.). FIG. 30 includes a front view (FIG. 30A) a side view (FIG. 30B), and a perspective view (FIG. 30C) of a track-based guidance system as described previously that incorporates additional guidance features 801, 802. The guidance features can be better seen in FIG. 30D in which a needle 839 is held in the features 801, 802 and in FIG. 30E in which the needle 839 is in the process of being removed from the features 801, 802.

Figure 30A:
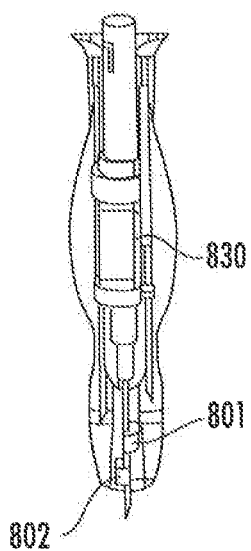
FIG. 30 illustrates a front view (FIG. 30A) a side view (FIG. 30B) and a perspective view (FIG. 30C) of a track-based guidance system including guidance features.
FIG. 30D illustrates a detailed view of the guidance features and FIG. 30E illustrates a method for removal of a needle from the grasp of the guidance features.
Figure 30B:
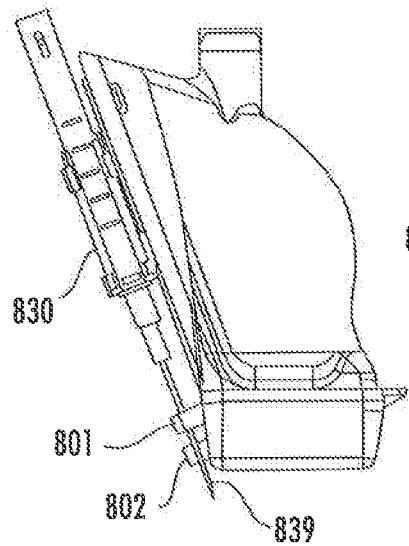
Figure 30C:
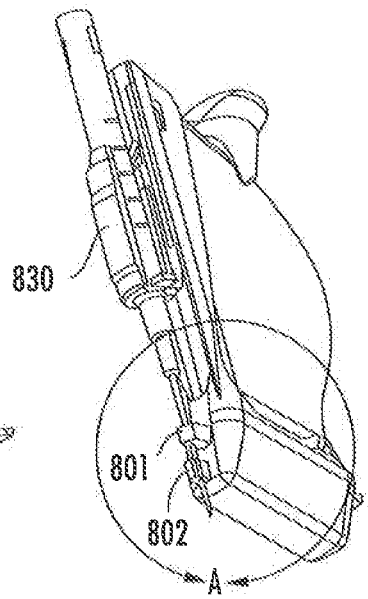
Figure 30D:
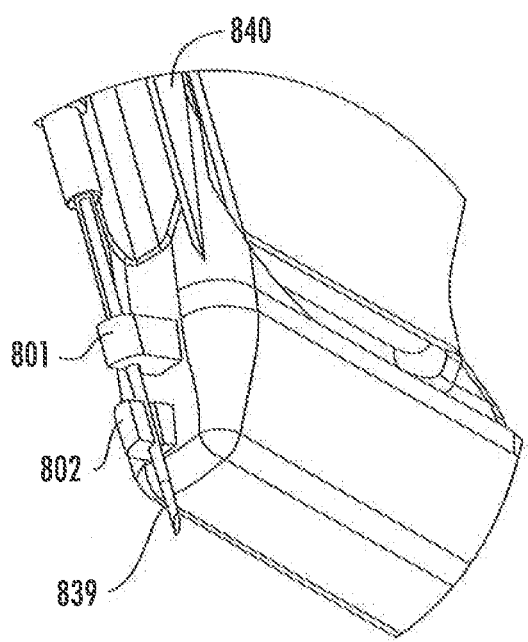
Figure 30E:
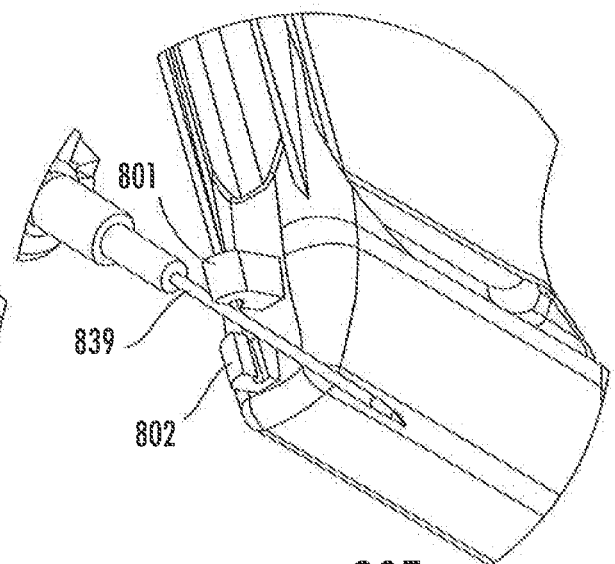

As a needle cartridge 830 slides down the guide track 840, the needle can be fed between the guidance features 801, 802 for stabilization. The guidance features can be formed of any suitable material such as a molded polymer. In one embodiment, the guidance features 801, 802 can be somewhat elastic in nature, which can facilitate removal of a subdermal device from the features. In one embodiment, the features can be retractable and can be pulled back away from the needle during retraction, which can be used to free the needle from the features. In the embodiment of FIG. 30, the guidance system can include two guidance features 801, 802 that can be spaced apart in the axial direction of the needle, which can facilitate removal of the needle from the features. In addition, the guidance features 801, 802 can be located such that a needle that is carried down the guidance track 840 can be fed between the two features. Optionally, the needle 839 can contact one or both of the features as it passes. As seen in FIG. 30E, the needle can be simply rotated out of the features 801, 802 for removal.

FIG. 31 includes a front view (FIG. 31A) a side view (FIG. 31B), and a perspective view (FIG. 31C) of a track-based guidance system as described previously that incorporates a single guidance features 901. The guidance feature can be better seen in FIG. 31D in which a needle 939 is held in the feature 901 and in FIG. 31E in which the needle 939 is in the process of being removed from the feature 901.

Figure 31A:
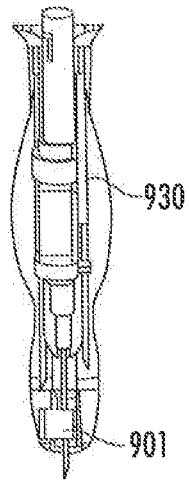
FIG. 31 illustrates a front view (FIG. 31A) a side view (FIG. 31B) and a perspective view (FIG. 31C) of a track-based guidance system including guidance features.
FIG. 31D illustrates a detailed view of the guidance features and FIG. 31E illustrates a method for removal of a needle from the grasp of the guidance features.
Figure 31B:
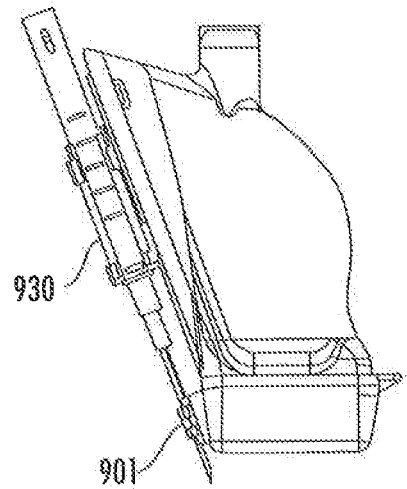
Figure 31C:
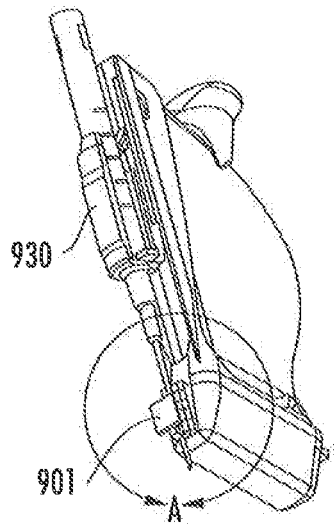
Figure 31D:
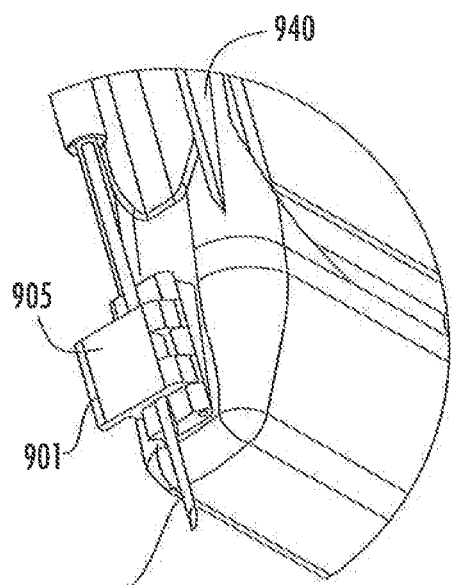
Figure 31E:
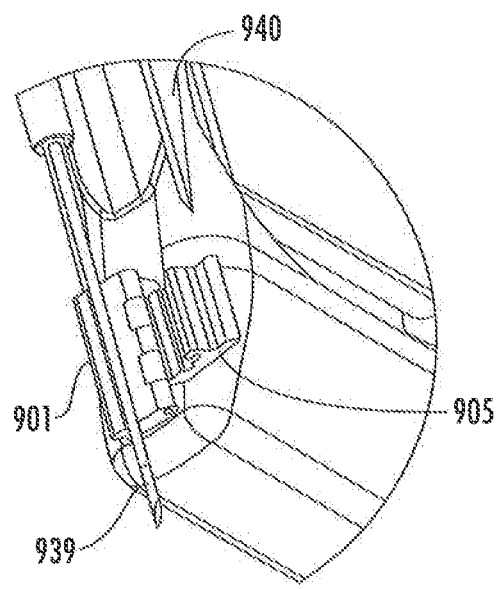

As a needle cartridge 930 slides down the guide track 940, the needle can be fed into the guidance feature 901 for stabilization. The guidance feature can include a hinged cover 905 that when closed can define a needle guide through the feature and upon opening as shown in FIG. 31E can release the needle 939.

Guidance features can be permanently or removably attached to the base of a sterilizable shield or shell that is used with a sterilizable seal and beneath other components of a guidance system (such as beneath the guidance track as illustrated). Thus, the tip of a subdermal device can pass through the guidance features after it exits the guidance track for additional stabilization prior to being inserted into the skin of a patient.

Following placement of a subdermal device at the internal target, the portion of the subdermal device that is still associated with the ultrasound device can be conveniently removed from the attached components. For instance, upon placement of the tip of the subdermal device at the target, the guidance cartridge may still be constrained within the guide rails of a guidance track. To separate the subdermal device, the guidance cartridge can be slid off of the guide rail(s) and lifted from the track for removal. In those embodiments that include additional guidance features at the base of the track, the subdermal device (e.g., the needle) can be removed from the guidance features by opening the feature, by rotation of the features and/or the subdermal device, by retraction of the features, etc. as necessary.

Presently disclosed ultrasound devices and methods may be utilized in many different medical procedures. Exemplary applications for the devices can include, without limitation Amniocentesis
Arthrocentesis
Biopsies (breast, kidney, liver, etc.)
Central Venous Catheterization
Cholecystic Drain Placement
Cardiac Catheterization (Central Arterial Access)
Diagnosis
Dialysis Catheter Placement
Epidural Catheter Placement
Imaging
Lumbar Puncture
Paracentesis
Pericardiocentesis
Peripherally Inserted Central Catheter (PICC) line placement
Regional Anesthesia - Nerve Block
Thoracentesis
Thyroid Nodule Biopsies Some of these exemplary procedures have employed the use of ultrasound devices in the past, and all of these procedures, as well as others not specifically listed, could utilize disclosed ultrasound devices to improve procedural safety as well as patient safety and comfort, in addition to provide more economical use of ultrasound devices.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A system for use in conjunction with an ultrasound device comprising:
a guide rail comprising a first surface, the guide rail defining an insertion path, the guide rail being directly or indirectly attachable to the ultrasound device, wherein upon said attachment, the guide rail is in a predetermined relationship with a scan plane of an imaging ultrasound transducer of the ultrasound device;
a guide cartridge comprising a second surface, the second surface conforming with the first surface such that upon said conformation, the guide cartridge is capable of moving from a first position to a second position along the insertion path; and
a target for a magnetic detection system, the target comprising a permanent magnet, the magnetic detection system being configured for locating a tip of a subdermal device, wherein the target is directly or indirectly attachable to the guide cartridge.

2. The system of claim 1, further comprising a sterilizable shield that is removably attachable to a housing containing the imaging ultrasound transducer, wherein the guide rail extends from a surface of the sterilizable shield.

3. The system of claim 2, wherein the sterilizable shield comprises a pliable drape.

4. The system of claim 1, further comprising an identification tag.

5. The system of claim 1, the magnetic detection system further comprising a sensor for the permanent magnet, wherein upon said conformation of the second surface with the first surface, the permanent magnet and the sensor are in electromagnetic communication with one another.

6. The system of claim 1, the system further comprising a subdermal device, wherein the subdermal device comprises a needle, a tube, a biopsy needle, or a blade.

7. The system of claim 1, further comprising a shell that is removably attachable to a housing containing the imaging ultrasound transducer, wherein the guide rail extends from a surface of the shell.

8. The system of claim 7, the system further comprising a sterilizable pliable drape.

9. The system of claim 1, wherein the guide rail extends from a surface of a housing containing the imaging ultrasound transducer.

10. The system of claim 1, wherein the insertion path intersects the scan plane of the imaging ultrasound transducer.

11. A system for use in conjunction with an ultrasound device comprising:
- a guide rail comprising a first surface, the guide rail defining an insertion path, the guide rail being directly or indirectly attachable to the ultrasound device, wherein upon said attachment, said guide rail is in a predetermined relationship with a scan plane of an imaging ultrasound transducer of the ultrasound device;
- a guide cartridge comprising a second surface, the second surface conforming with the first surface such that upon said conformation, the guide cartridge is capable of moving from a first position to a second position along the insertion path, the guide cartridge containing a hub;
- a subdermal device configured to be retained by the hub; and
- a target for a magnetic detection system, the target comprising a permanent magnet, the magnetic detection system being configured for locating a tip of the subdermal device, wherein the permanent magnet is directly or indirectly attachable to the hub or to the subdermal device.

12. The system of claim 11, wherein the hub is removably attachable to the guide cartridge.

13. The system of claim 11, the system further comprising the ultrasound device, the ultrasound device comprising a housing that contains a sensor for the permanent magnet and the housing further containing the imaging ultrasound transducer, wherein upon said conformation of the second surface with the first surface, the permanent magnet and the sensor are in electromagnetic communication with one another.

14. The system of claim 11, further comprising an identification tag.

15. The system of claim 11, wherein the subdermal device comprises a needle, a tube, a biopsy needle, or a blade.

16. The system of claim 11, further comprising a sterilizable shield that is removably attachable to a housing containing the imaging ultrasound transducer, wherein the guide rail extends from a surface of the sterilizable shield.

17. The system of claim 16, wherein the sterilizable shield comprises a pliable drape.

18. The system of claim 11, further comprising a shell that is removably attachable to a housing containing the imaging ultrasound transducer, wherein the guide rail extends from a surface of the shell.

19. The system of claim 18, the system further comprising a sterilizable pliable drape.

20. The system of claim 11, wherein the guide rail extends from a surface of a housing containing the imaging ultrasound transducer.

21. The system of claim 11, wherein the insertion path intersects the scan plane.

22. The system of claim 19, wherein the sterilizable pliable drape is configured for location between the shell and the housing.

23. The system of claim 11, wherein the first surface and the second surface each include a curved surface.

24. The system of claim 11, wherein the first surface and the second surface each include multiple faces.

25. the System of claim 24, wherein the first surface and the second surface interlock with one another.

26. The system of claim 8, wherein the sterilizable pliable drape is configured for location between the shell and the housing.

* * * * *